US011730875B2

(12) United States Patent
Christensen

(10) Patent No.: US 11,730,875 B2
(45) Date of Patent: Aug. 22, 2023

(54) DUAL DRAINAGE BAG, ASSEMBLIES, AND RELATED METHODS

(71) Applicant: SteriGear, LLC, Provo, UT (US)

(72) Inventor: Earl G. Christensen, Alpine, UT (US)

(73) Assignee: SteriGear, LLC, Provo, UT (US)

( * ) Notice: Subject to any disclaimer, the term of this patent is extended or adjusted under 35 U.S.C. 154(b) by 539 days.

(21) Appl. No.: 16/836,585

(22) Filed: Mar. 31, 2020

(65) Prior Publication Data

US 2020/0306421 A1    Oct. 1, 2020

Related U.S. Application Data

(60) Provisional application No. 62/938,452, filed on Nov. 21, 2019, provisional application No. 62/827,724, filed on Apr. 1, 2019.

(51) Int. Cl.
*A61M 1/00* (2006.01)
*A61G 7/05* (2006.01)

(52) U.S. Cl.
CPC ............. *A61M 1/69* (2021.05); *A61G 7/0503* (2013.01); *A61M 1/86* (2021.05); *A61M 2202/0014* (2013.01); *A61M 2205/3379* (2013.01)

(58) Field of Classification Search
CPC .......... A61J 1/10; A61J 1/2093; A61J 1/1462; A61J 1/16; A61J 1/00; A61J 1/14; A61J 9/001; B65D 81/3266; B65D 75/5861; B65D 33/01; B65D 31/04; B65D 5/00; B65D 75/525; B65D 75/566; B65D 77/003; B65D 77/06; B65D 81/2023; A61M 2207/00; A61M 1/69; A61M 5/14; B67D 3/0029; B67D 3/0038; B67D 3/0067; B29C 66/53262; B29C 66/72343
See application file for complete search history.

(56) References Cited

U.S. PATENT DOCUMENTS

| | | | |
|---|---|---|---|
| D200,807 S | 4/1965 | Mason | |
| 3,253,593 A | 5/1966 | Cronin, Jr. | |
| 3,545,671 A * | 12/1970 | Ross ................ | A61B 5/150221 604/410 |
| 3,554,256 A * | 1/1971 | Anderson ................. | A61J 1/10 604/416 |
| D221,911 S | 9/1971 | Ericson | |
| 3,680,560 A * | 8/1972 | Pannier, Jr ............ | A61M 1/604 604/320 |

(Continued)

FOREIGN PATENT DOCUMENTS

| | | |
|---|---|---|
| KR | 1020049022170 A | 3/2004 |
| WO | 2010045042 | 4/2010 |

OTHER PUBLICATIONS

European Search Report dated Feb. 20, 2018 for EP application 09821003.

(Continued)

*Primary Examiner* — Adam Marcetich

(74) *Attorney, Agent, or Firm* — Dorsey & Whitney LLP

(57) ABSTRACT

Devices used to collect bodily fluids are disclosed. The devices may include a fluid bag and a transformable hanger for mounting the fluid bag to a support structure such as a hospital bed rail. The fluid bag can include a first fluid compartment and a second fluid compartment. The devices may further include a displaceable front cover and a back cover to obscure the bodily fluids from observation.

19 Claims, 24 Drawing Sheets

(56) References Cited

U.S. PATENT DOCUMENTS

| | | | |
|---|---|---|---|
| 3,731,684 A | 5/1973 | Spiegel | |
| D227,184 S | 6/1973 | Stevens | |
| 3,973,565 A | 8/1976 | Steer | |
| 4,086,825 A | 5/1978 | Dodge | |
| 4,086,925 A | 5/1978 | Dodge | |
| 4,095,589 A | 6/1978 | Manschot et al. | |
| 4,122,851 A | 10/1978 | Grossner | |
| 4,153,163 A | 5/1979 | Alderman et al. | |
| 4,173,979 A | 11/1979 | Odis | |
| 4,188,989 A * | 2/1980 | Andersen | A61F 5/44 600/580 |
| 4,312,352 A | 1/1982 | Meisch | |
| 4,343,316 A | 8/1982 | Jespersen | |
| 4,401,239 A * | 8/1983 | Thomassen | B65D 77/065 229/117.27 |
| 4,417,892 A | 11/1983 | Meisch | |
| 4,460,362 A | 7/1984 | Bates | |
| 4,477,046 A * | 10/1984 | Repp | A61G 5/10 248/95 |
| 4,496,354 A | 1/1985 | Steer et al. | |
| 4,526,576 A | 7/1985 | Cianci | |
| 4,562,984 A | 1/1986 | Sherlock | |
| 4,606,736 A | 8/1986 | Van Den Weghe | |
| 4,625,734 A | 12/1986 | Sherlock | |
| D296,360 S | 6/1988 | Oelberg | |
| 4,787,222 A | 11/1988 | Irazoqui et al. | |
| 4,874,387 A | 10/1989 | Boone | |
| 4,886,674 A * | 12/1989 | Seward | B65D 85/8061 426/77 |
| 4,936,837 A | 6/1990 | Wexler | |
| 4,938,747 A | 7/1990 | Wallace | |
| D310,721 S | 9/1990 | Beisdang, III | |
| 4,955,879 A * | 9/1990 | Mervine | A61F 5/44 604/327 |
| 5,046,195 A | 9/1991 | Koritan | |
| 5,056,685 A | 10/1991 | Wild | |
| 5,211,642 A | 5/1993 | Clendenning | |
| 5,226,564 A | 7/1993 | Steer et al. | |
| 5,263,946 A | 11/1993 | Klug | |
| 5,454,797 A | 10/1995 | Haswell | |
| 5,489,281 A | 2/1996 | Watanabe et al. | |
| 5,496,299 A | 3/1996 | Felix et al. | |
| D369,662 S | 5/1996 | Kuentz | |
| 5,531,724 A | 7/1996 | Young | |
| D375,355 S | 11/1996 | Bierman | |
| D377,115 S | 1/1997 | Feriend et al. | |
| 5,686,096 A | 11/1997 | Khan et al. | |
| D391,483 S | 3/1998 | Freeman | |
| 5,725,515 A | 3/1998 | Propp | |
| 5,759,180 A | 6/1998 | Myhres | |
| D398,990 S | 9/1998 | Briggs et al. | |
| 5,865,793 A | 2/1999 | Lo et al. | |
| 6,053,905 A | 4/2000 | Daignault, Jr. et al. | |
| 6,096,007 A | 8/2000 | Haan et al. | |
| 6,132,407 A | 10/2000 | Genese et al. | |
| D438,616 S | 3/2001 | Williams | |
| 6,261,254 B1 | 7/2001 | Baron et al. | |
| D458,687 S | 6/2002 | Dale et al. | |
| 6,482,190 B1 | 11/2002 | Genese et al. | |
| D467,414 S | 12/2002 | Pavlu et al. | |
| D470,586 S | 2/2003 | Felstet | |
| 6,613,036 B1 | 9/2003 | Farmer et al. | |
| D482,063 S | 11/2003 | Jones et al. | |
| 6,709,420 B1 | 3/2004 | Lincoln et al. | |
| D502,557 S | 3/2005 | O'Dell | |
| 6,955,272 B2 | 10/2005 | Collins | |
| D515,699 S | 2/2006 | Girod | |
| 7,001,370 B2 | 2/2006 | Kubalak et al. | |
| D537,948 S | 3/2007 | Smith | |
| 7,210,994 B1 * | 5/2007 | Donohue | A61B 16/00 452/198 |
| D563,552 S | 3/2008 | Bierman et al. | |
| D577,437 S | 9/2008 | Bierman et al. | |
| 7,500,968 B1 | 3/2009 | Nappa et al. | |
| 7,513,894 B2 | 4/2009 | Howlett | |
| D601,707 S | 10/2009 | Chouiller | |
| 7,645,968 B2 | 1/2010 | Salvadori et al. | |
| D609,802 S | 2/2010 | Harren | |
| D612,060 S | 3/2010 | Smith | |
| D612,937 S | 3/2010 | Christensen | |
| D621,926 S | 8/2010 | Christensen | |
| 8,092,436 B2 | 1/2012 | Christensen | |
| D673,266 S | 12/2012 | Tufts et al. | |
| 8,361,044 B2 | 1/2013 | Marshall | |
| D684,687 S | 6/2013 | Christensen | |
| D684,688 S | 6/2013 | Christensen | |
| 2001/0030134 A1 * | 10/2001 | Goglio | B65D 81/3266 383/69 |
| 2002/0066678 A1 * | 6/2002 | Sharon | B65D 81/3266 206/568 |
| 2002/0077609 A1 | 6/2002 | Johnson | |
| 2002/0193761 A1 | 12/2002 | Lord | |
| 2003/0060786 A1 | 3/2003 | Olsen et al. | |
| 2004/0147887 A1 | 7/2004 | Hagstroem et al. | |
| 2004/0236293 A1 | 11/2004 | Tanghoj et al. | |
| 2004/0240520 A1 | 12/2004 | Faries et al. | |
| 2005/0059952 A1 | 3/2005 | Giuliano et al. | |
| 2005/0103653 A1 * | 5/2005 | Eckhardt | A23D 7/02 206/219 |
| 2006/0111681 A1 | 5/2006 | Vernon | |
| 2007/0199453 A1 * | 8/2007 | Rasmussen | B65D 85/816 99/279 |
| 2007/0203463 A1 | 8/2007 | Salvadori et al. | |
| 2007/0203464 A1 | 8/2007 | Green et al. | |
| 2007/0282296 A1 | 12/2007 | Matsuda et al. | |
| 2009/0024099 A1 | 1/2009 | Burgess et al. | |
| 2009/0030384 A1 * | 1/2009 | Christen | A61M 1/604 604/319 |
| 2009/0030386 A1 | 1/2009 | Kim et al. | |
| 2009/0036861 A1 | 2/2009 | Moy et al. | |
| 2009/0088709 A1 | 4/2009 | Salvadori | |
| 2009/0283541 A1 * | 11/2009 | Compton | B65D 77/068 222/105 |
| 2011/0087181 A1 | 4/2011 | Bidwell et al. | |
| 2011/0238022 A1 | 9/2011 | Massi et al. | |
| 2012/0041400 A1 | 2/2012 | Christensen | |
| 2012/0082403 A1 * | 4/2012 | Zyburt | A61F 5/445 383/42 |
| 2013/0319575 A1 * | 12/2013 | Mendyk | A61J 1/1475 141/94 |
| 2014/0287104 A1 * | 9/2014 | Austin | A47J 31/369 426/115 |
| 2014/0336598 A1 | 11/2014 | Christensen | |
| 2017/0081111 A1 * | 3/2017 | Wicks | B65D 85/8061 |
| 2020/0155735 A1 | 5/2020 | Christensen | |

OTHER PUBLICATIONS

International Search Report and Written Opinion dated Apr. 27, 2010 for international application PCT/US2009/059482.

"Drainage Bag Cover", Western Home Medical; www.westernhomemedical.com/product.jsp?product_id=83; accessed May 30, 2008 (1 page).

"Privacy Cover for Urinary Drainage Bags; Access to Recreation", www.store.accesstr.com/Detail.bok?no=1789 accessed May 30, 2008 (1 page).

"SteriGear Fig Leaf Urinary Drain Bag", as shown on http://long-term-care.advancedweb.com, dated Oct. 2, 2009 (2 pages).

"Urinary Drain Bag with Fig Leaf Cover by SteriGear", Urinary Drain Bag with Fig Leaf Cover by SteriGear as shown on www.SteriGear.com, viewed Jan. 13, 2010 (1 page) pub date unknown.

"Urine Drain Bag Holder", http://cgi.ebay.ca/Urine-Drain-bag-holder-Disceet-Catheter-Bag-Cover_WOQQitemZ320 . . . ; accessed May 30, 2008 (4 pages).

Christensen , Notice of Allowance dated Dec. 14, 2015 for U.S. Appl. No. 29/534,458.

Christensen , Notice of Allowance dated Feb. 14, 2013 for U.S. Appl. No. 29/390,343.

Christensen , Notice of Allowance dated Feb. 14, 2013 for U.S. Appl. No. 29/390,346.

(56) References Cited

OTHER PUBLICATIONS

Christensen, Notice of Allowance dated Mar. 20, 2014 for U.S. Appl. No. 13/088,409.
Christensen, Notice of Allowance dated Sep. 29, 2011 for U.S. Appl. No. 12/253,714.
Christensen, Office Action dated Apr. 11, 2014 for U.S. Appl. No. 29/390,348.
Christensen, Office Action dated Aug. 7, 2019 for U.S. Appl. No. 14/444,271.
Christensen, Office Action dated Dec. 16, 2013 for U.S. Appl. No. 13/088,409.
Christensen, Office Action dated Feb. 13, 2020 for U.S. Appl. No. 14/444,271.
Christensen, Office Action dated Jan. 25, 2019 for U.S. Appl. No. 14/444,271.
Christensen, Office Action dated Jan. 29, 2015 for U.S. Appl. No. 29/390,348.
Christensen, Office Action dated Jul. 25, 2013 for U.S. Appl. No. 29/390,348.
Christensen, Office Action dated Jul. 27, 2017 for U.S. Appl. No. 14/444,271.
Christensen, Office Action dated Oct. 18, 2016 for U.S. Appl. No. 14/444,271.
Christensen, Office Action dated Sep. 12, 2013 for U.S. Appl. No. 13/088,409.
PCT/US2009/059482, International Preliminary Report on Patentability, dated Apr. 19, 2011, 4 pages.
International Search Report and Written Opinion dated Jun. 23, 2020 for international application PCT/US2020/026008.
Partial European Search Report dated Nov. 10, 2022 received in European patent application No. 20782271.9.
Extended European Search Report dated Feb. 10, 2023 issued in European patent application No. 20782271.9.
International Search Report and Written Opinion dated Jun. 23, 2020 received in international patent application No. PCT/US2020/026008.

* cited by examiner

US 11,730,875 B2

DUAL DRAINAGE BAG, ASSEMBLIES, AND RELATED METHODS

RELATED APPLICATIONS

This application claims priority to U.S. Provisional Patent Application No. 62/827,724, filed Apr. 1, 2019, and titled DUAL DRAINAGE BAG, ASSEMBLIES, AND RELATED METHODS, and U.S. Provisional Patent Application No. 62/938,452, filed Nov. 21, 2019, and titled DUAL DRAINAGE BAG, ASSEMBLIES, AND RELATED METHODS, each of which is incorporated herein by reference in its entirety.

TECHNICAL FIELD

The present disclosure relates generally to the field of medical devices. More specifically, the present disclosure relates to bodily fluid drainage assemblies and related methods of use.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

DETAILED DESCRIPTION

A fluid drainage assembly may include a fluid bag configured to receive bodily fluid drained from a site within a human body, such as a bladder. The fluid bag may include various components, such as an inlet port configured to couple to a drainage tube, an outlet tube having an output regulator, one or more fluid compartments, one or more air vents (which can allow passage of gas or air into and/or out of the fluid compartments), and/or a volume indicator. In some instances, each fluid compartment may include transparent or translucent front and/or back panels. Each fluid compartment may also include a displaceable cover to obscure observation of the bodily fluid collected within the fluid compartment or fluid bag. In certain instances, the drainage assembly may include a transformable hanger coupled to the fluid bag and configured to suspend the fluid bag from a support structure, such as a bed rail. The hanger may be configured to transform configurations such that either the first fluid compartment or the second fluid compartment faces outward toward a clinician. In doing so, the fluid drainage assembly can be disposed at various locations on a support structure (e.g., bed or chair structure), and on either side of the support structure (e.g., bed or chair structure).

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure but is merely representative of various embodiments. While the various aspects of the embodiments are presented in drawings, the drawings are not necessarily drawn to scale unless specifically indicated.

It will be appreciated that various features are sometimes grouped together in a single embodiment, figure, or description thereof for the purpose of streamlining the disclosure. Many of these features may be used alone and/or in combination with one another.

The phrase "coupled to" refers to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

"Fluid" is used in its broadest sense, to refer to any fluid, including both liquids and gases as well as solutions, compounds, suspensions, etc., which generally behave as fluids.

Figure 1:
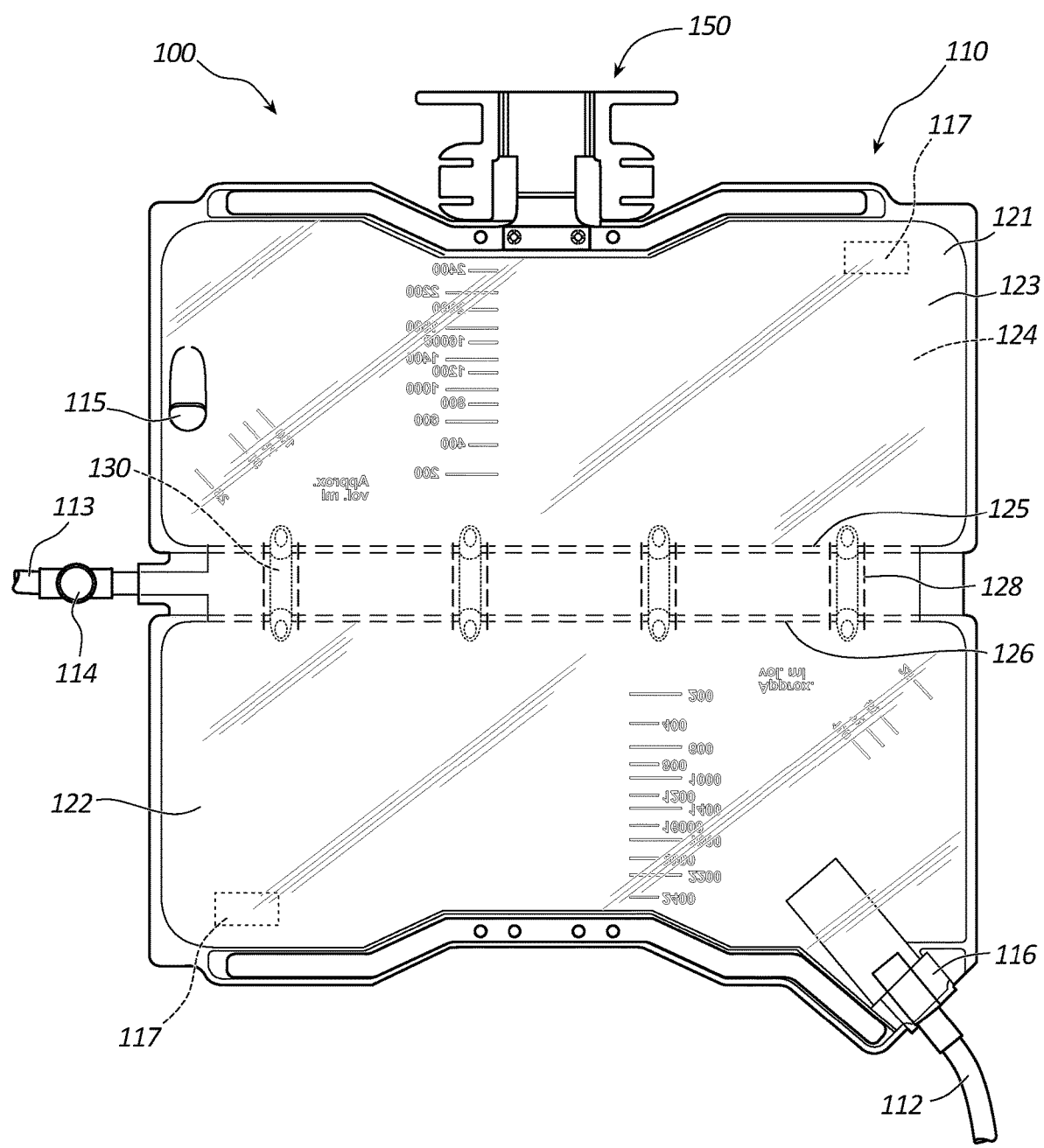
FIG. 1 is a plan view of a bodily fluid drainage assembly, depicted in an unassembled configuration.

FIG. 1 depicts a bodily fluid drainage assembly 100 in an unassembled configuration or state. The bodily fluid drainage assembly 100 includes a drainage bag assembly 110 and a hanger 150. The drainage bag assembly 110 includes one or more fluid compartments 121, 122. The fluid compartments 121, 122 can also be referred to as fluid bags or fluid receptacles. As detailed below, the drainage assembly 100 is configured to receive bodily drainage fluid; retain the drainage fluid; and/or selectively drain the drainage fluid from the drainage assembly 100. In some embodiments, the drainage assembly 100 is also configured to at least partially obscure the visibility of the drainage fluid while allowing an approximate volume of the fluid to be determined; and/or optionally allow the fluid to be directly viewed by at least partially displacing or removing a portion of the drainage assembly 100.

In the embodiment of FIG. 1, the drainage bag assembly 110 includes a first fluid compartment 121 and a second fluid compartment 122. The fluid compartments 121, 122 are in fluid communication with one another, such that fluid from one compartment 121, 122 can flow to and from the other compartment 121, 122. The flow can be unobstructed and free of interference. For instance, fluid from the first fluid compartment 121 can flow to the second compartment 122 and vice versa. At least one of the fluid compartments 121, 122 comprises an inlet port 116. At least one of the fluid compartments 121, 122 can comprise an air vent 117. Further, in some embodiments, each of the fluid compartments 121, 122 comprises an air vent 117. The air vent 117 can allow for air and/or gas to flow into and/or out of the fluid compartments 121, 122. For example, air and/or gas can be released from the fluid compartment 121, 122 as it fills with bodily fluid. Air and/or gas can also flow into the fluid compartment 121, 122 as the bodily fluid is drained from the fluid compartment 121, 122.

As shown in FIG. 1, the fluid compartments 121, 122 may comprise a front or first panel 123 and a back or second panel 124, which may be made of one or more liquid impervious materials. For example, the front and back panels 123, 124 may be formed from polyvinyl chloride, polyurethane, vinyl, polymeric, or any other suitable material. At least a portion of the front and back panels 123, 124 can be substantially transparent or translucent such that a drainage fluid contained within the fluid compartments 121, 122 may be readily observed. The panels 123, 124 may be coupled or joined along a peripheral edge thereof via radio frequency (RF) welding, heat sealing, gluing, or any other suitable technique. When coupled together, the panels 123, 124 form a fillable void that may receive drainage fluid via a drainage tube 112 and a corresponding inlet port 116 that are located on an upper portion of at least one of the fluid compartments 121, 122. The panels 123, 124 can also be flexible rather than rigid, such that the fluid compartments 121, 122 can expand as they fill with drainage fluid.

Figure 8:
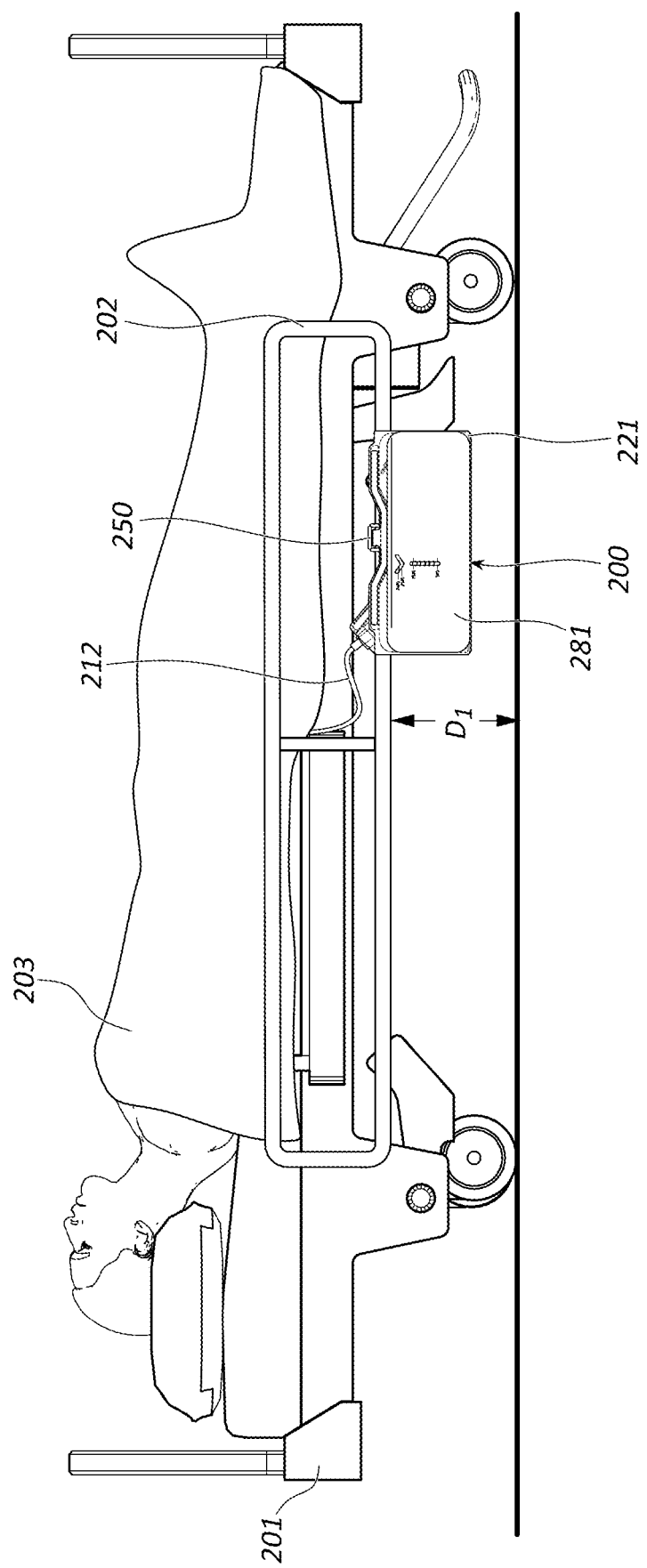
FIG. 8 is a front view of a bodily fluid drainage assembly mounted to a hospital bed rail.
Figure 9:
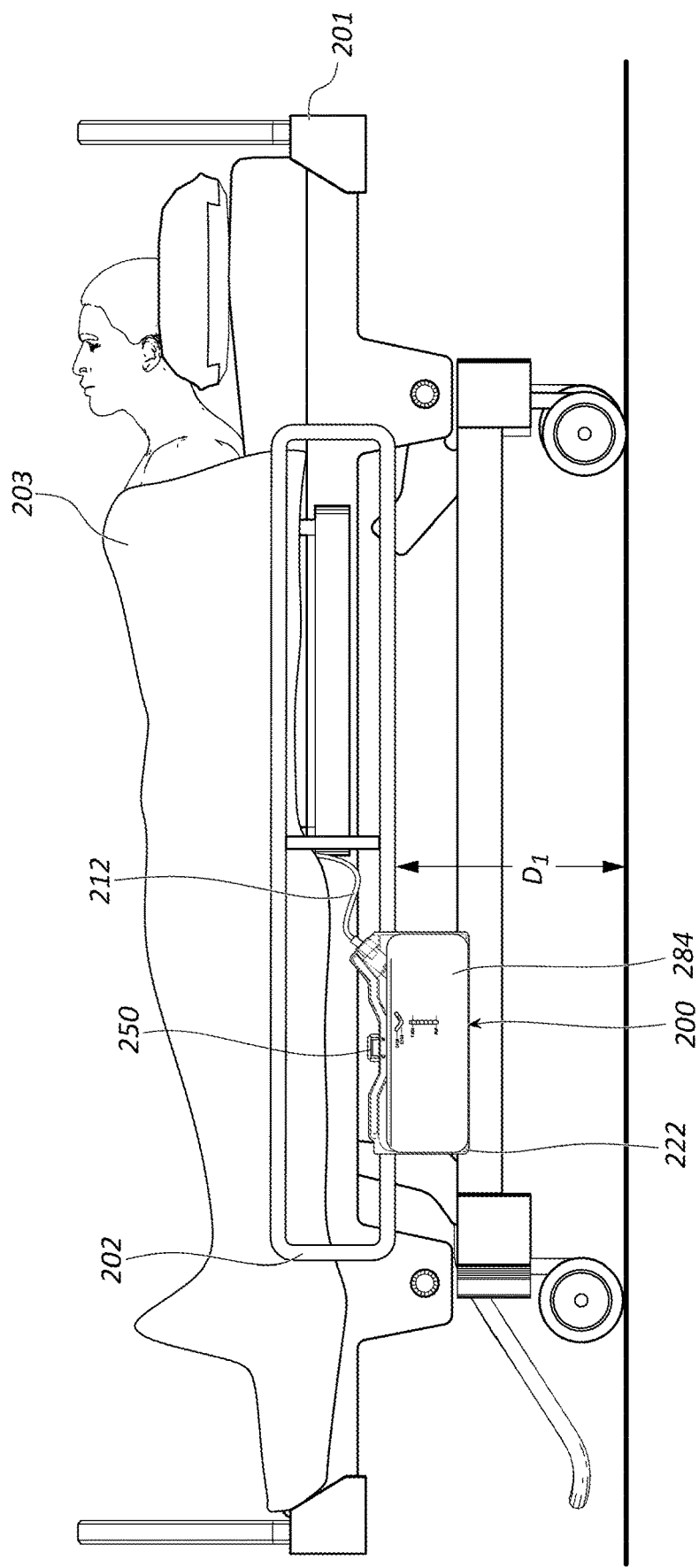
FIG. 9 is a front view of a bodily fluid drainage assembly mounted to a hospital bed rail opposite of the hospital bed rail of FIG. 8.

It will further be appreciated that a variety of types and configurations of fluid bags can be utilized without departing from the scope and spirit of the present disclosure. For example, the fluid compartments 121, 122 may be manufactured using a one-piece method, wherein the fluid compartments 121, 122 comprise a single piece of plastic that is folded along one or more edges and, further, is sealed to itself or otherwise closed along one or more edges. A two-piece manufacturing method can also be used, wherein two separate panels are coupled together. Further, the shape and size of drainage assembly 100 is primarily for illustrative purposes and may vary. In the depicted embodiment, the drainage bag assembly 110 is configured in a horizontal or landscape configuration where the height of the bag is less the width of the bag. This configuration allows for the drainage bag assembly 110 to be hung from a support, such as a hospital bed rail, that may be located as low as approximately seven inches from a floor surface—as illustrated in FIGS. 8-9 where $D_1$ may be lowered to less than 18 inches, less than 12 inches, less than 10 inches, or less than 8 inches (e.g., when the bed is in the lowered state).

As further shown in FIG. 1, the first and second fluid compartments 121, 122 can be defined by one or more seams 125, 126 that extend across a central region of the drainage bag assembly 110. For instance, the illustrated embodiment includes a first seam 125 and a second seam 126 that are disposed between the first and second fluid compartments 121, 122. The seams can be made in various ways, such as via radio frequency (RF) welding, heat sealing, gluing, or any other suitable technique. The seams 125, 126 can also be discontinuous, such that they do not block the flow of fluid between the fluid compartments 121, 122. For example, the seams 125, 126 can be referred to as spot seams (or spot welds).

The seams 125, 126 can couple one or more portions of the panels 123, 124 together. The seams 125, 126 can also define fold regions along which the drainage bag assembly 110 folds when assembled. In other embodiments, the first and second fluid compartments 121, 122 are defined by fold lines, as the drainage bag assembly 110 can be folded to form two halves or fluid compartments 121, 122 (which can double the volume of fluid for a given bag height).

In certain embodiments, the drainage bag assembly 110 further includes one or more conduits 130 that can be configured to communicate with each of the fluid compartments 121, 122. In such embodiments, fluid can flow through the conduits 130 and between the fluid compartments 121, 122. The conduits 130 can be disposed within the drainage bag assembly 110, and can be held in place via one or more seams 128, which can be formed in various ways, such as via radio frequency (RF) welding, heat sealing, gluing, or any other suitable technique. The conduits 130 can also be held in place by an adhesive, such as a glue. In other embodiments, conduits 130 are not used.

As illustrated, an outlet tube 113 can also be disposed between the fluid compartments 121, 122. The outlet tube 113 may allow the drainage fluid contained within the fluid compartments 121, 122 to be selectively drained from or retained within the fluid compartments 121, 122 via an output regulator 114. The output regulator 114 may comprise a plastic or metal clip, in-line valve, rotatable valve, or any other suitable structure. At least one of the fluid compartments 121, 122 may further comprise an outlet tube holder 115 that comprises a slot, loop, pocket, or hook that is configured to receive and reversibly retain outlet tube 113 in an at least partially upright or folded position. For example, in the illustrated embodiment, the outlet tube holder 115 comprises a plastic tube so as to define a cavity. When the drainage assembly 100 is in use or a pre-use state, a bottom end of the outlet tube 113 can be positioned within the cavity of the outlet tube holder 115. The outlet tube 113 can be removed from the outlet tube holder 115 and allowed to hang downwardly into the extended position shown in FIG. 7 during drainage of fluid from the fluid compartments 121, 122.

Figure 2:
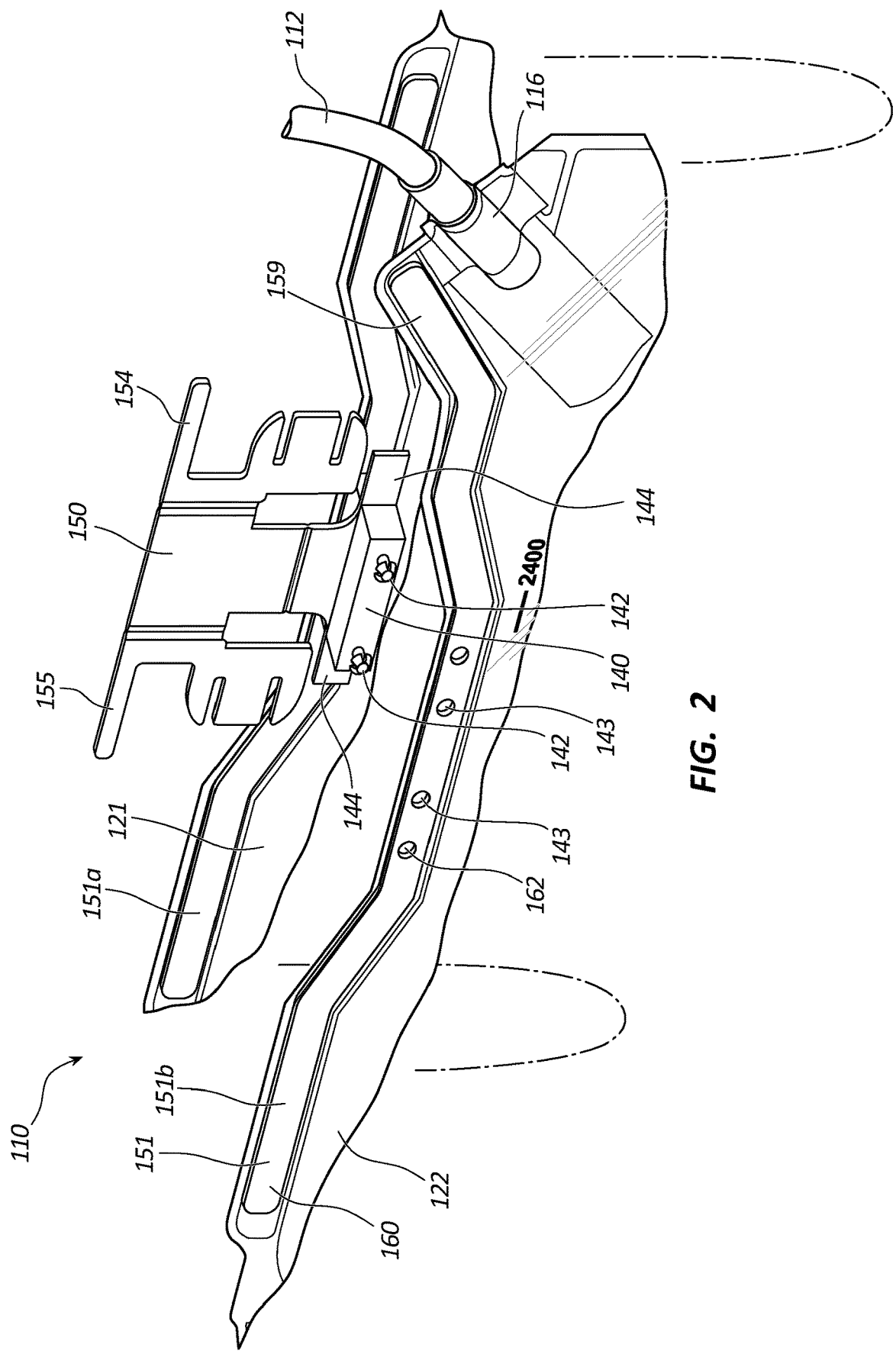
FIG. 2 is a partial view of the bodily fluid drainage assembly of FIG. 1, depicted as it is being assembled.
Figure 3:
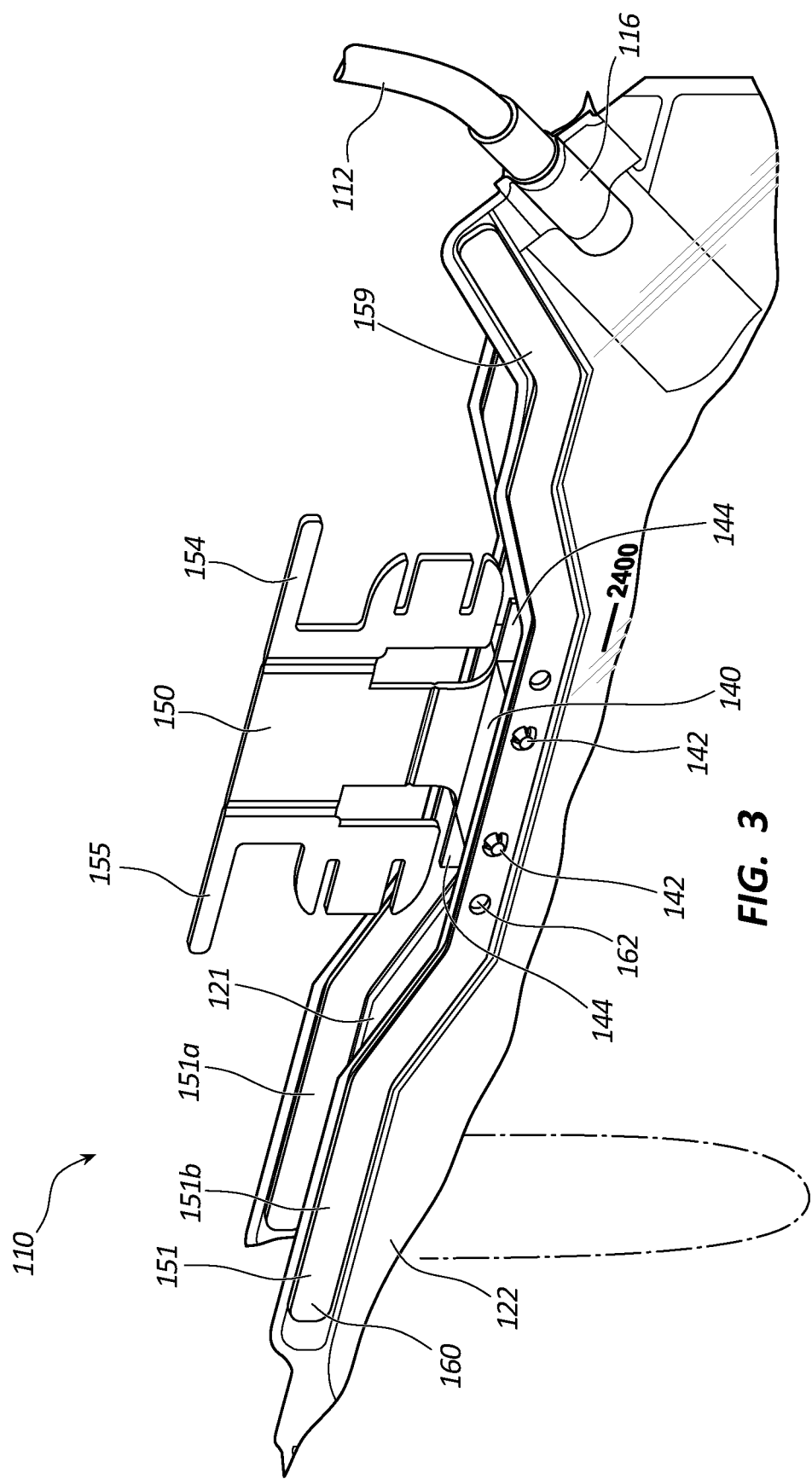
FIG. 3 is a partial view of the bodily fluid drainage assembly of FIG. 1, depicted in an assembled configuration.
Figure 4:
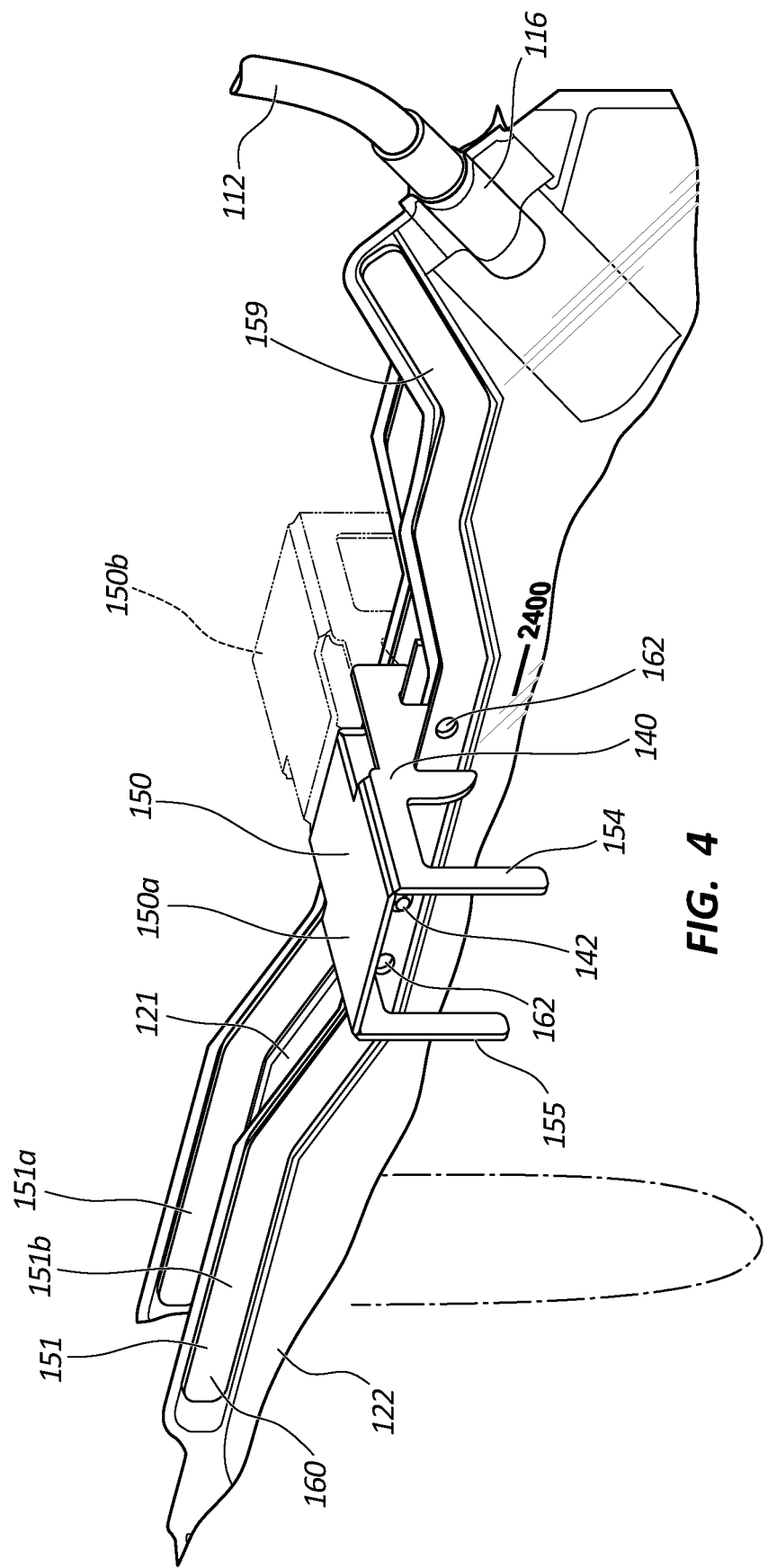
FIG. 4 is a partial view of the bodily fluid drainage assembly of FIG. 3, depicted with a hanger in a folded state.

The drainage bag assembly 110 can be folded and/or assembled prior to use. For example, as shown in FIGS. 2-4, the drainage bag assembly 110 can be folded such that the first fluid compartment 121 and the second fluid compartment 122 are parallel to one another, or side by side. In some embodiments, the drainage bag assembly 110 is folded along seams 125, 126 or predetermined fold lines. The first fluid compartment 121 can also be coupled to the second fluid compartment 122 such that the drainage bag assembly 110 can remain in the folded or assembled configuration.

For instance, as shown in FIG. 2, the drainage bag assembly 110 includes a base or brace 140 that extends between the first and second fluid compartments 121, 122. The brace 140 can be coupled to an elongate member 151 of each of the first and second fluid compartments 121, 122. For instance, with reference to FIGS. 2-4, each of the first and second fluid compartments 121, 122 includes an elongate member 151. In some embodiments, the elongate member 151 may be configured as a non-linear, elongate bar. In other embodiments, the elongate member 151 may be configured as a linear, elongate bar. In some instances, the elongate member 151 can also include horizontal and angled segments that permit the elongate member 151 to avoid interference with features of the drainage bag assembly 110, such as the inlet port 116 and the air vent 117 when used with or coupled to the fluid compartments 121, 122. For example, a portion 159 of the elongate member 151 may extend toward the inlet port 116 and may include two horizontal segments and two angled segments. As another example, another portion 160 of the elongate member 151 may extend toward the air vent 117 and may include two horizontal segments and an angled segment disposed between the horizontal segments. The elongate member 151 may also include at least one retention feature 162. The retention feature 162 may be configured to retain the wings 154, 155 of the hanger 150 in a folded or deployed state as illustrated in FIG. 4. The retention feature 162 may be in the form of a bump, ridge, nub, boss, etc. or any other suitable form.

In FIG. 2, the brace 140 is shown coupled to the first elongate member 151a and uncoupled from the second elongate member 151b. The brace 140 can be coupled to each of the elongate members 151a, 151b in an analogous manner, or in a different manner, as desired. For instance, the brace 140 can include one or more coupling members 142 that can couple to each of the elongate members 151. Thus, while only one side of the brace 140 is depicted in the illustrated embodiment, it will be appreciated that the opposite side of the brace 140 can be configured in a similar manner if desired.

The coupling members 142 can be configured to couple to the elongate member 151 in various ways. For instance, in the illustrated embodiment, the elongate member 151 includes complementary coupling members 143 that are configured to mate with or otherwise couple with the coupling members 142 of the brace 140. In some instances, the coupling of the brace 140 to the elongate member 151 is non-reversible, such that the elongate members 151 (and/or fluid compartments 121, 122) are not intended to be unassembled or uncoupled from the brace 140 after being coupled thereto. With reference to FIG. 2, for instance, the brace 140 includes first coupling members 142 that are configured to be inserted into and/or received by second coupling members 143 of the second elongate member 151b. Once inserted, the coupling members 142, 143 can be formed such that they are not intended to be uncoupled (e.g., such as in a snap fit engagement). Various types of coupling members 142, 143 can be used, including mating coupling members, latches, buttons, snap-fit engagements, and the like. In other embodiments, the brace 140 can be reversibly coupled to the one or more elongate members 151.

FIGS. 3 and 4 depict the drainage bag assembly 110 in an assembled configuration. As shown in FIG. 3, the coupling members 142 of the brace 140 have been inserted into the coupling members of the elongate member 151. The drainage bag assembly 110 further includes a hanger or rail clip 150. The hanger or rail clip 150 can be coupled to or disposed on the brace 140. For example, in the illustrated embodiment of FIGS. 3 and 4, the hanger 150 can be positioned and extend from the brace 140.

The hanger 150 can be configured to allow the drainage assembly 100 to be suspended from a patient, or from a support structure, such as a wheelchair, bed, a bed rail, or stand. As shown in FIG. 4, the hanger can be positioned such that it is directed towards either side of the drainage bag assembly 110. For instance, the hanger 150b can be positioned towards the first fluid compartment 121, or the hanger 150a can be positioned towards the second fluid compartment 122, as desired by the practitioner (e.g., a practitioner may suspend the drainage assembly 100 in either direction, depending on a desired orientation of the inlet port 116 and tube 112.)

Figure 5A:
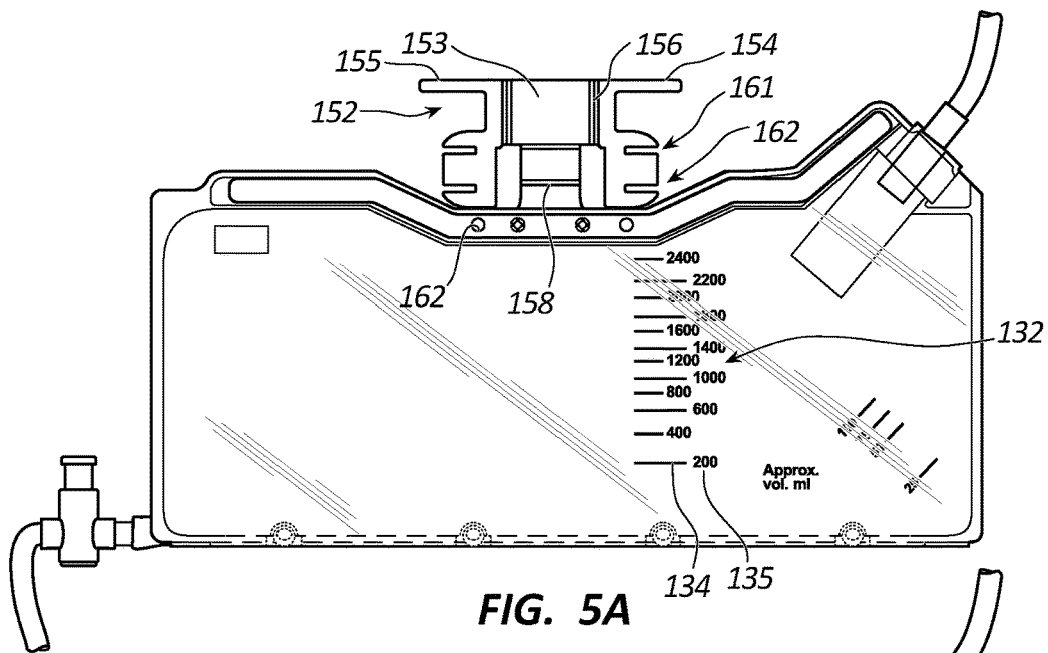
FIG. 5A is a front view of the bodily fluid drainage assembly of FIG. 3, depicted with the hanger in an unfolded state.
Figure 5B:
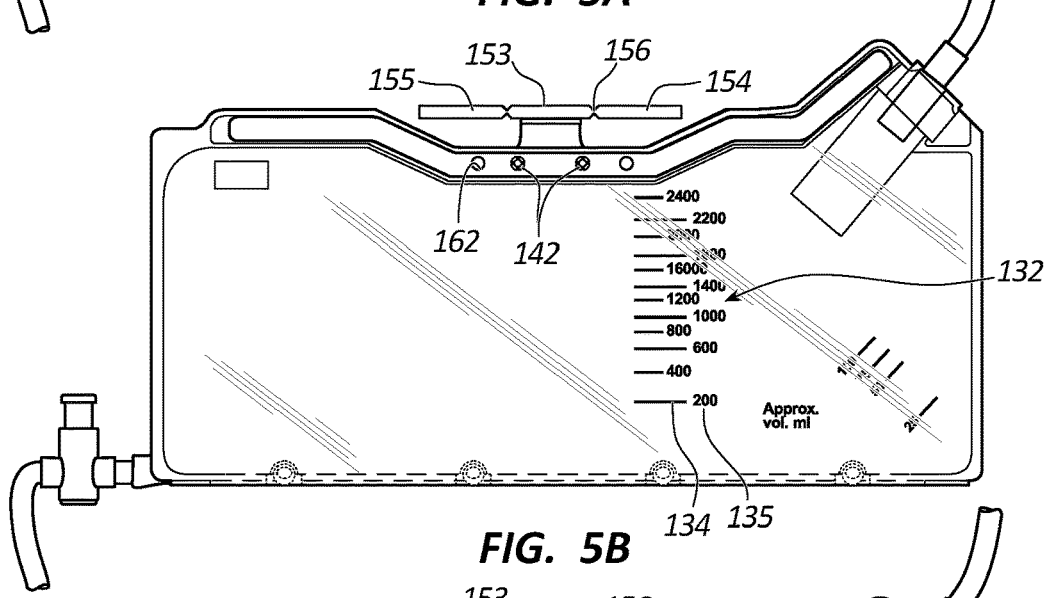
FIG. 5B is a front view of the bodily fluid drainage assembly of FIG. 3, depicted with the hanger in partially folded state.
Figure 5C:
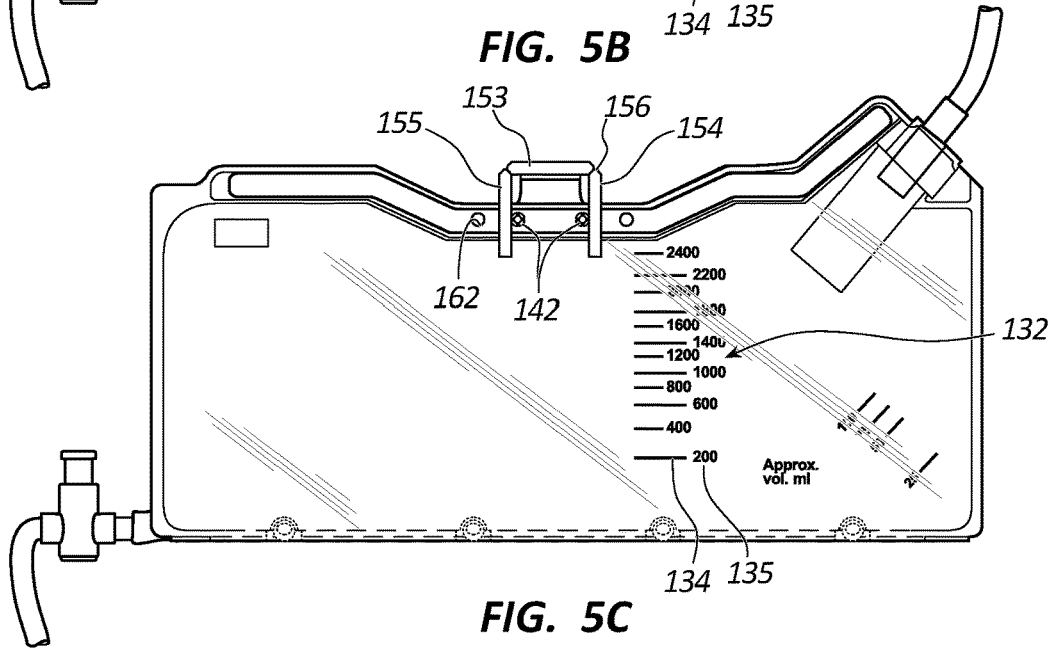
FIG. 5C is a front view of the bodily fluid drainage assembly of FIG. 3, depicted with the hanger in a folded state.

As illustrated in FIGS. 5A-5C, the hanger 150 may include a central portion 153, a first laterally extending member or wing 154, and a second laterally extending portion or wing 155. The hanger 150 may be formed as an integral unit using any suitable manufacturing technique, such as injection molding, casting, machining, etc. In other embodiments, the hanger 150 may be assembled from separate components using any suitable assembly technique.

The hanger 150 may be formed from any suitable material, such as a polymeric material like polypropylene, polyethylene, blends thereof, etc.

The central portion 153 may be coupled to the brace 140 and may also include a flexible or living hinge 158 such that a face of the central portion 153 is oriented parallel to a vertical axis or plane of the elongate members 151 in an undeployed state, as illustrated in FIG. 5A. The living hinge 158 may allow the central portion to pivot or fold about the living hinge 158 approximately or at least 180 degrees relative to the vertical axis or plane of the elongate member 151 (e.g., at least 90 degrees in either direction). In other words, the central portion 153 may be pivoted from a vertical orientation to a horizontal orientation on either side of the elongate member 151 when the hanger 150 is deployed, as depicted in FIGS. 5B-5C.

The first and second wings 154, 155 may be coupled to the central portion 153 via a flexible or living hinge 156 such that the wings 154, 155 are oriented in a plane of the face of the central portion 153 in the undeployed state, as shown in FIGS. 5B-5C. The living hinge 156 may allow the wings 154, 155 to pivot or fold about the living hinge 156 approximately or at least 180 degrees relative to the plane of the face of the central portion 153 (e.g., at least 90 degrees in either direction). In other words, the wings 154, 155 may be pivoted from the parallel orientation to a perpendicular orientation on either side of the central portion 153 when the hanger 150 is deployed, as depicted in FIG. 4. The wings 154, 155 may include a support receiver 152 configured to be clipped over or disposed over a portion of a hospital bed rail. In other embodiments, the support receiver 152 may be configured to be clipped over or disposed over any suitable support, such as a wheelchair, a stand, etc. In certain embodiments, adjacent edges of the elongate member 151, central portion 153 and wings 154, 155 may be radiused or double beveled to facilitate pivoting or folding.

As shown in the depicted embodiment, the wings 154, 155 may also include an elongate member receiver or elongate member section receiver 161. The elongate member receiver 161 may have a substantially U-shaped form where a portion of the elongate member 151 can be removably disposed within the elongate member receiver 161 when the hanger 150 is deployed. In some instances, the retention feature(s) 162 can also aid in retaining the wings 154, 155 in a folded or deployed state. For example, the wings 154, 155 can be forced over the retention feature(s) 162 as the hanger 150 is folded or deployed. The retention feature(s) 162 can then retain the wings 154, 155 in the folded or deployed state absent application of an outside force to unfold the wings 154, 155.

In certain embodiments, the wings 154, 155 may further include brace extension receiver 162. The brace extension receiver 162 may also have a substantially U-shaped form where a portion of the brace extension 144 can be removably disposed within the brace extension receiver 162 when the hanger 150 is deployed. The brace extensions 144 can protrude from the brace 140 and can be configured to further aid in retaining and/or supporting the hanger when in a deployed or folded state. The brace extension 144 can also include retention features if desired.

As previously discussed, in the illustrated embodiment, the hanger or rail clip 150 is configured to be oriented either toward the first fluid compartment 121 or the second fluid compartment 122 when deployed. This dual orientation capability of the hanger 150 permits the drainage assembly 100 to be suspended from a support, such as a bed rail, with either the first fluid compartment 121 or the second fluid compartment 122 directed outwardly toward a viewer. Additionally, the dual orientation capability allows the viewer to orient the drainage assembly 100 at various locations along a support structure (e.g., upwards (towards the head) or downwards (towards the feet) from the bladder of a patient) or on either side of the support structure (e.g., bed structure) and still have the drainage port 116 adjacent a patient's drainage site in order to route the drainage tube 112 easily to the drainage site.

In some embodiments, an approximate volume of drainage fluid within the fluid bag 111 may be ascertained via a bag volume indicator 132, which may comprise marks or graduations 134, 135 on at least one panel 124 of each of the fluid compartments 121, 122. In the depicted embodiment, graduations 134, 135 denote various predetermined volumes and may be printed on each of the fluid compartments 121, 122. In another embodiment, the graduations 134, 135 may comprise raised or recessed portions of the fluid compartments 121, 122 that are formed during or after manufacturing of the each of the fluid compartments 121, 122. The graduations 134, 135 may represent any predetermined measurement of volume, such as fluid ounces and/or milliliters, and may vary in their relative distributions accordingly. In some embodiments, the space between sequential graduations 134, 135 may not be uniform in scale so as to account for a non-linear rate of rise in fluid level, such as may result from expansion of the fluid compartment 121, 122 as the fluid compartment 121, 122 fills with drainage fluid and/or from a transverse dimension of the fluid compartment 121, 122 that varies with a height of the bag. In the depicted embodiment, the graduations 134, 135 are located on a right portion (as seen from the viewer's perspective) of the fluid compartment 121, 122; however, in other embodiments, the graduations may be located at any suitable location on the fluid compartment 121, 122. In the illustrated embodiment, the volume indicator 132 also extends upwardly. Since at least a portion of the fluid compartment 121, 122 is transparent or semitransparent (e.g., translucent), the top of the drainage fluid can be compared to the graduations 134, 135 to thereby determine the volume of the fluid, or the approximate volume thereof.

Figure 6A:
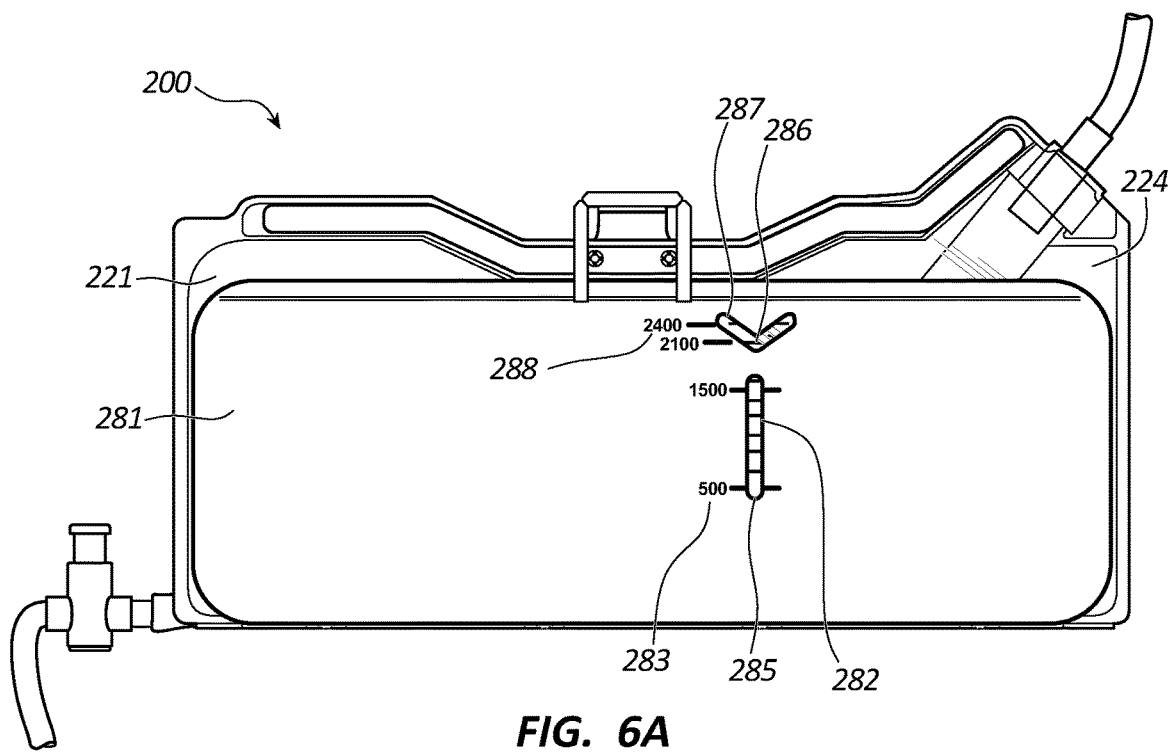
FIG. 6A is a front view of a bodily fluid drainage assembly, depicted with a cover.
Figure 6B:
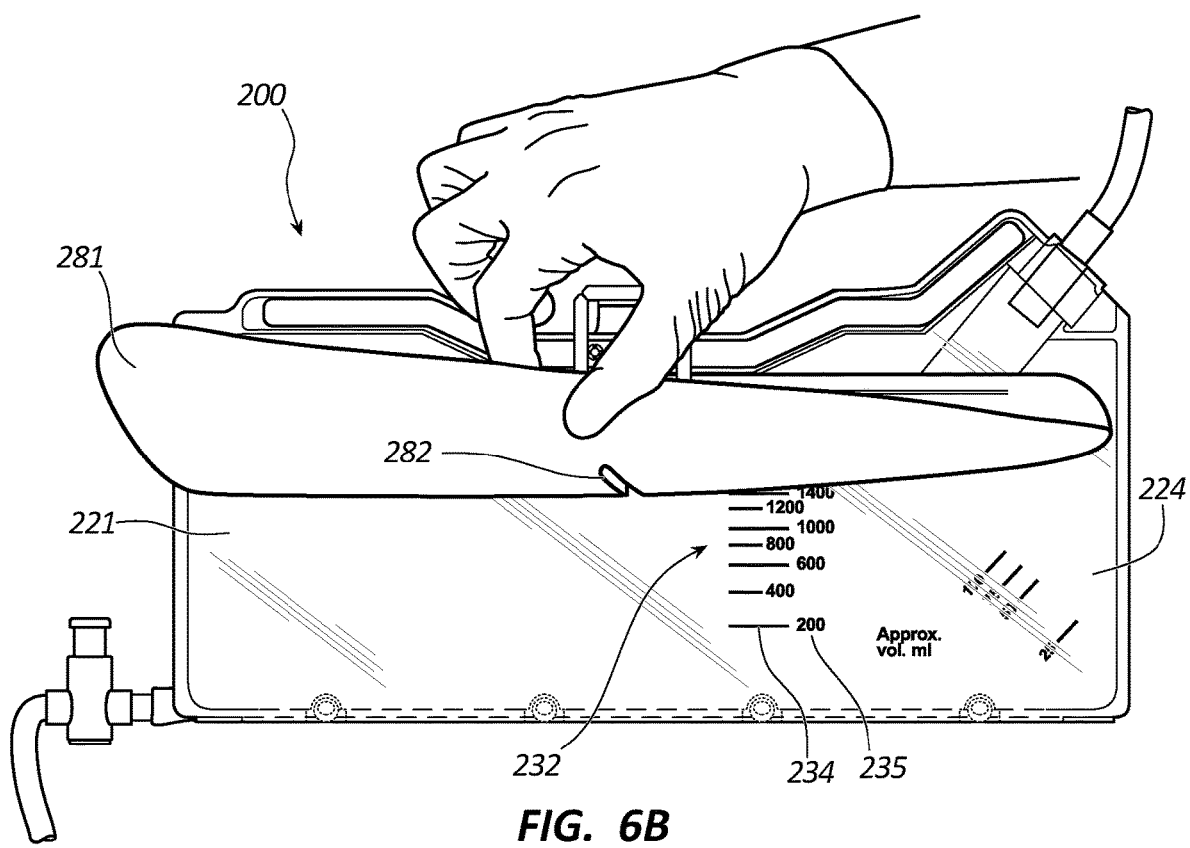
FIG. 6B is a front view of the bodily fluid drainage assembly of FIG. 6A, depicted with the cover partially lifted.

As shown in FIGS. 6A and 6B, in certain embodiments, one or more (or both) of the fluid compartments 221 further comprises a cover 281 that can be formed from or otherwise include an opaque material (or at least partially opaque material capable of obscuring the appearance of a fluid positioned at one side thereof), and that may define a similar shape as the fluid compartment 221. For example, the cover 281 may be formed from polyvinyl chloride, polyurethane, vinyl, polymeric, or any other suitable material. As depicted, the cover 281 is located adjacent to and is configured to obscure the fluid compartment 221. A second cover (not depicted) can also be disposed on an opposite side of the bag and in front of the second fluid compartment. The covers 281 have an outer edge that may be at least partially aligned with an outer edge of the fluid compartments 221. However, at least a portion of the outer edge of the covers 281 may extend outwardly beyond the outer edge of the fluid compartment 221, if desired.

The cover 281 can be coupled or attached to the fluid compartment 221 in any suitable manner, such as RF welding, heat sealing, gluing, hardware, etc. In the illustrated embodiment, the cover 281 is fixedly attached to the fluid compartment 221 along a seam which extends along an upper edge of the cover 281. The seam may provide an area or region of weakness along which the cover 281 may be readily removed from the fluid compartment 221, if desired. Other regions of weakness (e.g., perforations) may also be used.

The cover 281 may be said to be integral with the fluid compartment 221. For example, in some embodiments, the drainage assembly 200 is sterilized and packaged with all of the components shown in FIG. 6A. While it may be possible to remove the cover 281 from the drainage assembly 200, as just discussed, the cover 281 is nevertheless a fixed and permanent component of the drainage assembly 200. For example, if the cover 281 is removed by pealing it along its region of weakness, a portion of the cover 281 (generally the portion that is attached to the panels 221 by the seam) can nevertheless remain attached to the fluid compartment 221. In other embodiments, the cover 181 can be selectively attachable to and detachable from the drainage assembly 200, such as with snaps, hook-and-loop fasteners, adhesives, or any other suitable temporary fastening system. For example, the fasteners can be positioned along an upper edge of the cover 281.

As previously mentioned, the cover 281 is coupled or attached to the drainage assembly 200 at an upper end of the fluid compartment 221. The cover 281 thus naturally hangs or drapes downward so as to be positioned in front of the face of the panel 224 and/or fluid compartment 221. The cover 281 can thus conceal or obscure viewing of a large portion of the panel 224 and/or fluid compartment 221, when the drainage assembly 200 is viewed from a position in front of or behind the drainage assembly 200. A lower edge of the cover 281 may not be attached to the fluid compartment 221 such that at least a portion of the cover 281 may be lifted to expose the fluid compartment 221 and its contents. In other embodiments, the lower edge of the cover 281 may be selectively attached to the fluid compartment 221. Such selective attachment and detachment may be achieved in any suitable manner, such as via snaps, hook-and-loop fasteners, adhesives, or other suitable releasable fastening system. In other embodiments, a cover can be configured as a slip cover that is disposed over the fluid bag assembly. For instance, a polymeric or fabric cover can be disposed over the fluid bag assembly rather than coupled thereto.

The cover 281 can include one or more volume indicators 285. The illustrated first volume indicator 285 includes a window 282 and one or more graduations 283. A variety of configurations for the window 282 and the graduations 283 are possible. For example, a variety of shapes are possible for the window 282, and the number and arrangement of the graduations 283 may be varied. In the illustrated embodiment, the window 282 defines a permanent opening through the cover 281 and is fully encompassed by solid or unbroken portions of the cover 281. The window 282 defines a small, vertically oriented longitudinal slot. Only a small portion of the fluid compartment 221 is visible through the window 282 when the cover 281 are in the obscuring orientation. An approximate volume level can be determined when a top level of the drainage fluid is visible through the window 282, such as by comparing the level of the drainage fluid to the graduations 283. Due to the fixed relationship between the upper end of the cover 281 and the fluid compartment 221, the graduations 283 can provide a substantially accurate assessment of the approximate liquid volume when the cover 281 hangs downwardly.

In the illustrated embodiment, the window 282 may be oriented such that a portion of the graduations 234, 235 that are on the fluid compartment 221 are visible through the window 282 when the cover 281 are in the obscuring orientation. In certain embodiments, the bag graduations 234, 235 may be offset relative to the cover graduations 283 when the fluid compartment 221 is devoid of fluid. The offset can account for relative movement between the cover 281 and the fluid compartment 221 as the fluid compartment 221 fills with fluid. In particular, the fluid compartment 221 can transition from a generally flat configuration to an outwardly expanded or bowed configuration as it fills with the drainage fluid, and in some arrangements, the cover 281 may not strictly match the contour of the fluid compartment 281 as it expands. This relative shift in positions can cause the graduations 283 of the first volume indicator 285 to come into greater alignment with the graduations 234, 235 of the bag volume indicator 232.

The cover 281 may include a second volume indicator 286. The second volume indicator 286 includes a recess, such as a notch or cutout 287, and a set of graduations 288. A bottom end of the cutout 287 is at a position that is horizontally offset and/or spaced vertically from an upper end of the window 282. Due to the difference in vertical positions between the cutout 287 and the window 282, a top level of the drainage fluid can remain below the cutout 287 at all times that the window 282 is used in determining the approximate volume of the drainage fluid, and the top level of the drainage fluid can remain above the window 282 at all times that the cutout 287 is used in determining the approximate volume of the drainage fluid.

Each of the window 282 and the cutout 287 may be referred to as an aperture or opening in the cover 281 through which a portion of the panel 224 of the fluid compartment 221 may be directly viewed. The window 282 and the cutout 287 may be formed in any suitable manner, such as, for example, by stamping, cutting, or punching.

By way of further explanation, in the illustrated embodiment, the cover 281 is formed of a flexible material. When the drainage assembly 200 is in the unfilled state, the fluid compartment 221 can be substantially planar or flat, and the cover 281 can hang substantially vertically and may likewise be substantially planar or flat. The cover 281 may be positioned exclusively forward of the panel 224, and it may obscure an entirety of the panel 224 or fluid compartment 221 (except for those portions that are visible through the window 282 and the cutout 287) from all or nearly all vantage points that are forward of the drainage assembly 200. A second cover (not depicted) may be positioned exclusively behind the second fluid compartment, and it may obscure an entirety of the second fluid compartment (except for those portions that are visible through a window and a cutout) from all or nearly all vantage points that are rearward or backward of the drainage assembly 200.

In FIG. 6A, the cover 281 is shown in an obscuring (e.g., draped or lowered) orientation. In other words, the cover 281 is shown obscuring at least a portion of the panel 224 and/or fluid compartment 221. In FIG. 6B, the cover 281 is shown in a viewing (e.g., raised) orientation. In other words, the lower edge of the cover 281 is shown lifted to reveal at least a portion of the panel 224 and/or fluid compartment 221. A second cover can be configured to function in a similar manner relative to the second fluid compartment. It is noted that the term "obscuring orientation," when used with respect to the cover 281, does not necessarily connote that an entirety of the panel 224 and/or fluid compartment 221 is obscured (e.g., blocked or guarded from view, rendered difficult to view, or provided with a significantly altered appearance) by the cover 281. Indeed, as demonstrated by the embodiment depicted in FIG. 6A, restricted portions of the panel 224 and/or fluid compartment 221 can be viewed, observed, or visualized through the window 282 and the cutout 287 when the cover 281 is in the obscuring orientation.

Figure 7:
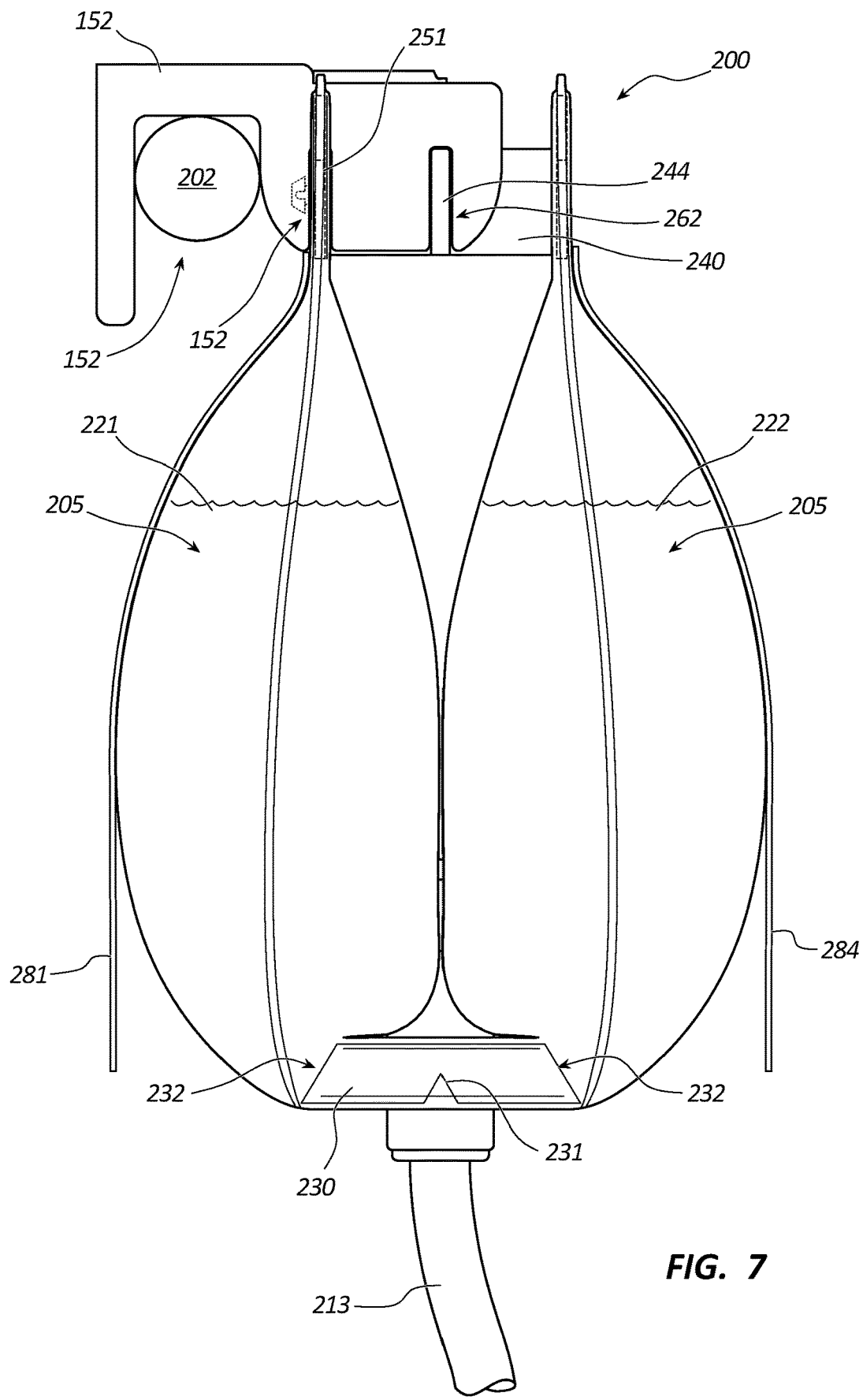
FIG. 7 is an end view of the bodily fluid drainage assembly of FIG. 6A.

FIG. 7 depicts an end view of a drainage assembly 200 that includes first and second fluid compartments 221, 222 each having a cover 281, 284 coupled thereto. As shown in FIG. 7, the covers 281, 284 drape over the outwardly facing surfaces of the first and second fluid compartments 221, 222. In such a manner, fluid 205 within the fluid compartments 221, 222 can be obscured from view by an observer. A bottom portion of the covers 281, 284 can also be lifted as desired to view the fluid 205 within the fluid compartments 221, 222.

The drainage assembly 200 further includes a hanger 250 that is configured to couple to a rail 202 or other structure. In the illustrated embodiment, the hanger 250 is depicted in a folded configuration or state, wherein the support receiver 262 is disposed over a rail 202. Additionally, the elongate member receiver 261 is depicted as being disposed over an elongate member 251 of the first fluid compartment 221, and the brace extension receiver 162 is depicted as being disposed over a brace extension 244 of the brace 240.

Additionally, FIG. 7 depicts a conduit 230 in communication with the first and second fluid compartments 221, 222. Fluid 205 can flow through a lumen 232 in the conduit 230 such that the fluid level in each of the fluid compartments is substantially the same. The conduit 230 also includes a notch or opening 231 such that fluid can flow out of the conduit 230 and towards the drainage tube 213. One or more conduits 230 can be used. Other structures can also be used to ensure flow is not substantially restricted (and can flow freely) between the fluid compartments 221, 222.

FIGS. 8-9 depict the drainage assembly 200 in use with a patient 203. As shown therein, the drainage assembly 200 may be suspended from a bed rail 202 that is coupled to a hospital bed 201. As discussed previously, the bed rail 202 may be positioned adjacent the floor such that a distance from the bed rail 202 to the floor is distance $D_1$. In some embodiments, as depicted in FIG. 8, the hospital bed 201 is configured to be lowered to be adjacent the floor (which can minimize a fall distance if a patient 203 falls out of the hospital bed 201). For instance, $D_1$ may be lowered to less than 18 inches, less than 12 inches, less than 10 inches, or less than 8 inches (e.g., when the bed 201 is in the lowered state). Stated another way, the bed 201 may be lowered such that $D_1$ is between about 6 and about 18 inches, between about 6 and about 12 inches, between about 6 and about 10 inches, or between about 6 and about 8 inches. In such embodiments, the drainage assembly 200 can be suspended from the bed rail 202 such that it does not touch the floor, even while the hospital bed 201 is in the lowered state. The hanger 250 can be folded to permit the hospital bed 201 to be lowered closer to the floor because of the low-profile configuration of the deployed hanger 250.

Figure 10:
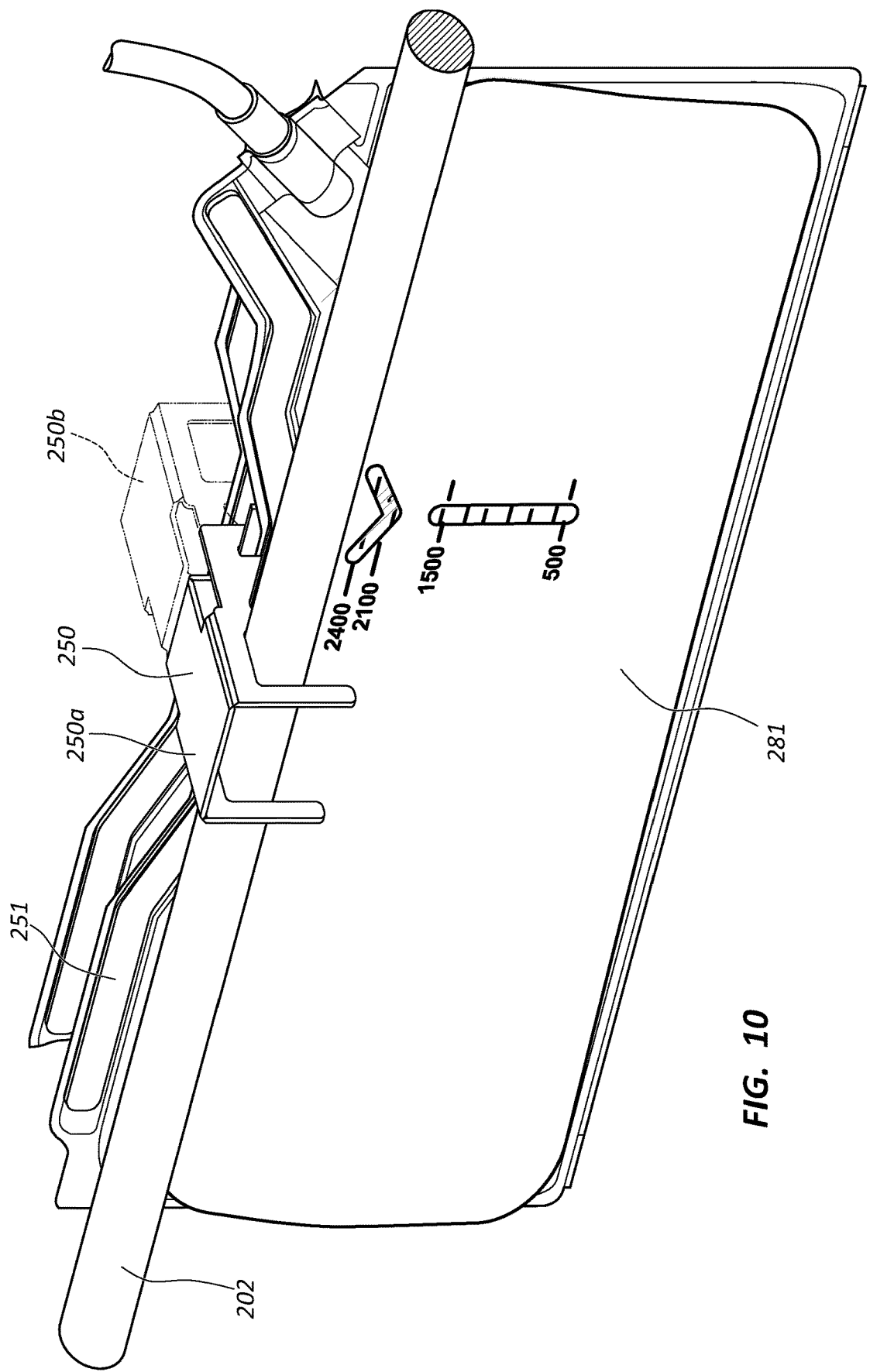
FIG. 10 is a front view of a bodily fluid drainage assembly mounted to a rail or support structure.
Figure 11A:
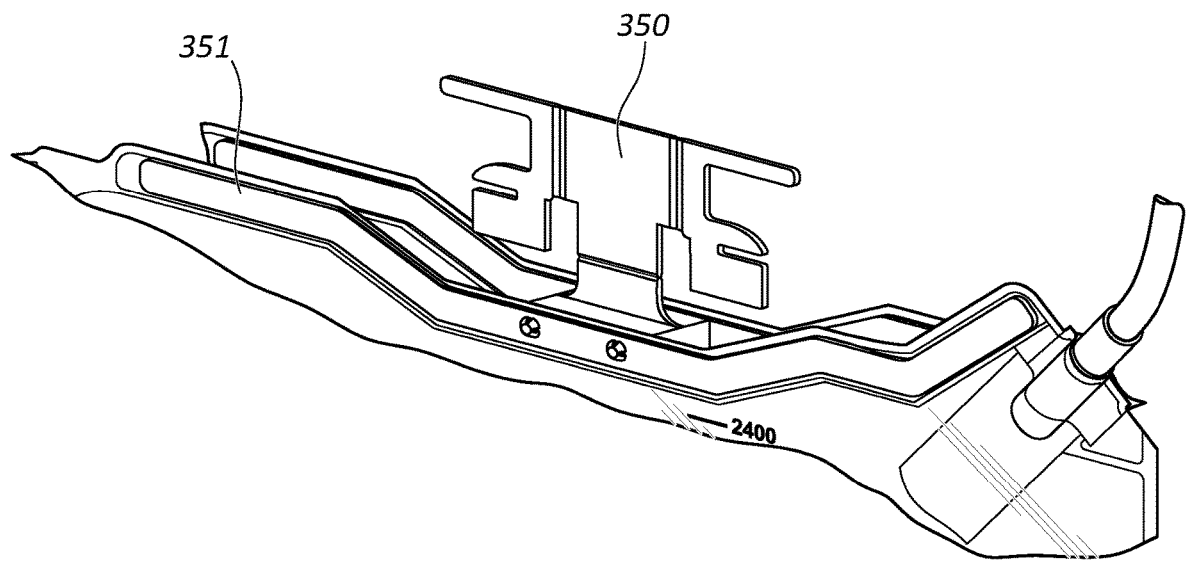
FIG. 11A is a partial view of a bodily fluid drainage assembly, depicted with a hanger in an unfolded state.
Figure 11B:
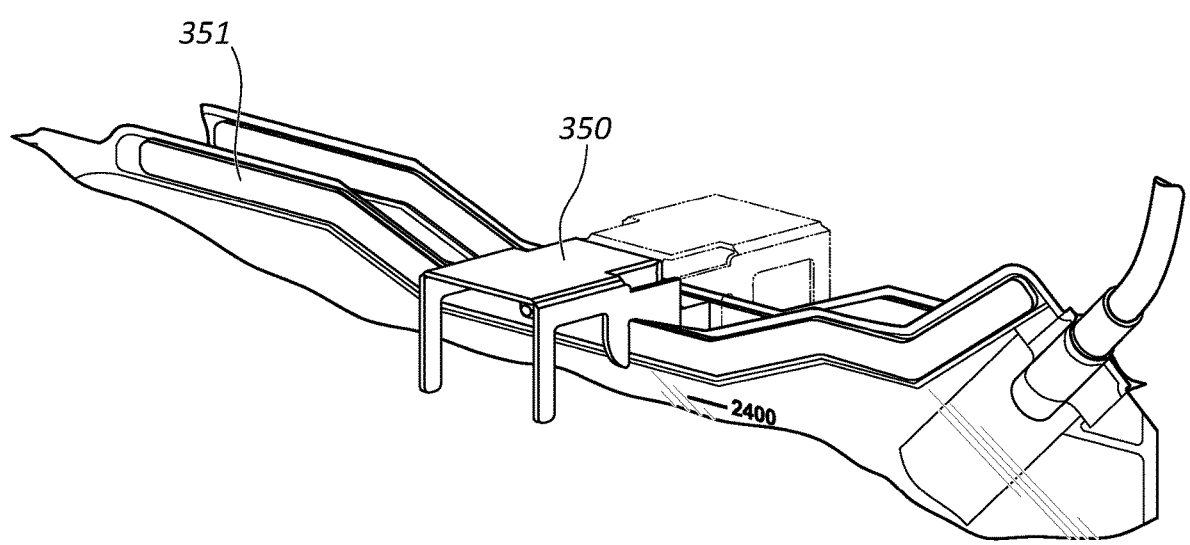
FIG. 11B is a partial view of the bodily fluid drainage assembly of FIG. 11A, depicted with the hanger in a folded state.
Figure 12A:
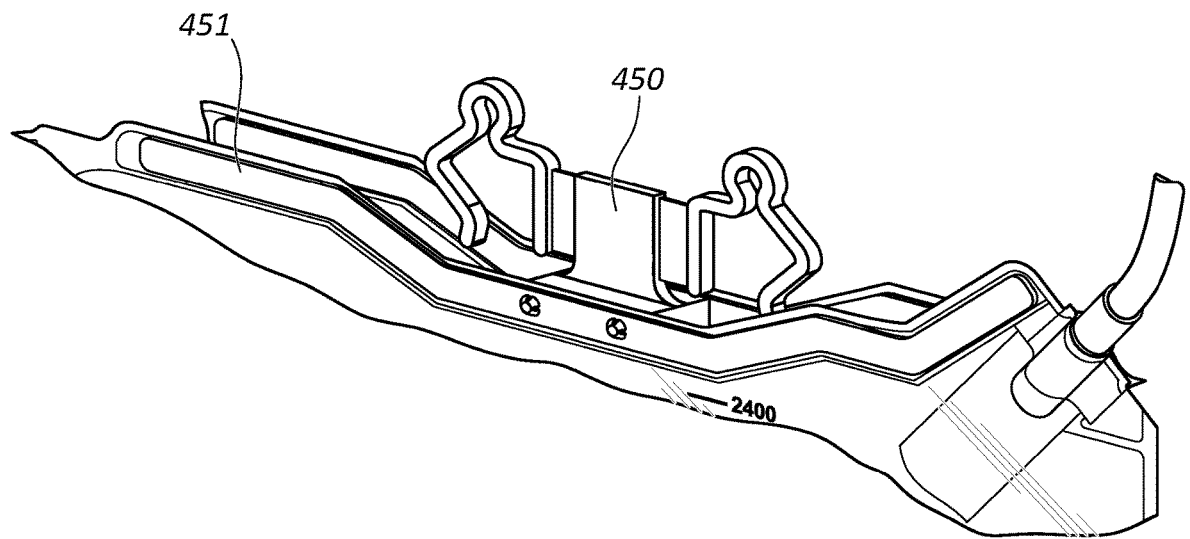
FIG. 12A is a partial view of a bodily fluid drainage assembly, depicted with a hanger in an unfolded state.
Figure 12B:
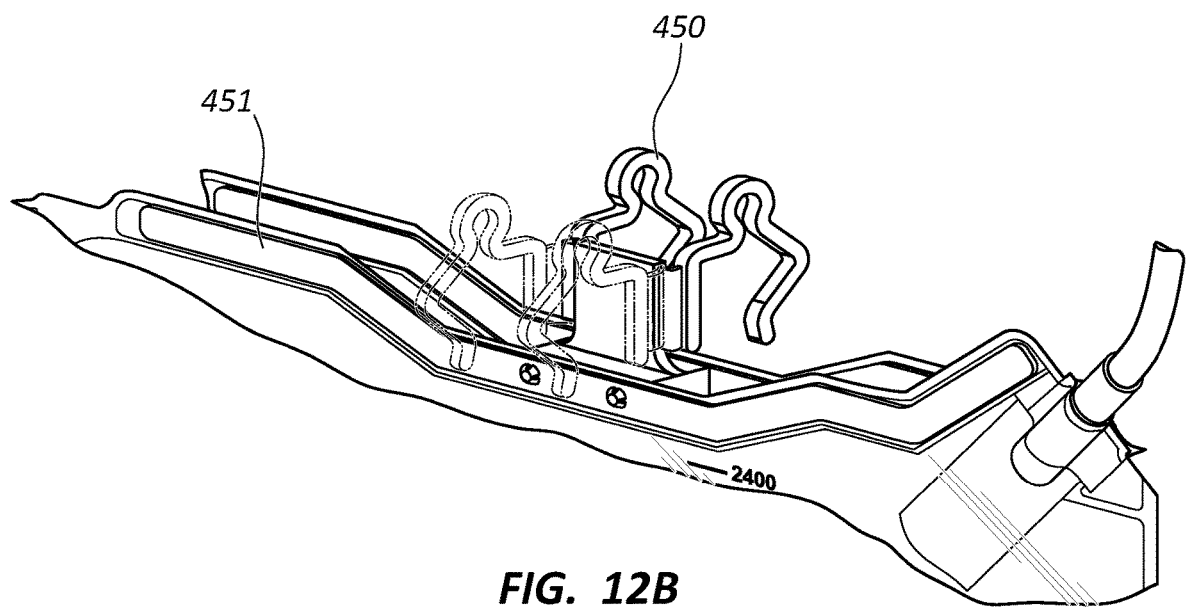
FIG. 12B is a partial view of the bodily fluid drainage assembly of FIG. 11A, depicted with the hanger in a folded state.

The drainage assembly 200 may also be oriented on either side of the bed structure 201 (or at various locations along the bed rail 202 (e.g., more towards the head or more towards the feet of the patient 203), such that either the first fluid compartment 221 and the first cover 281 are directed outwardly as shown in FIG. 8 (which depicts a first side of the hospital bed 201 or bed rail 102) or such that the second fluid compartment 222 and the second cover 284 are directed outwardly as shown in FIG. 9 (which depicts a second or opposite side of the hospital bed 201 or bed rail 202). For example, the hanger or rail clip 250 may be deployed such that the hanger 250 is oriented toward the second fluid compartment 222 when the first fluid compartment 221 is directed outwardly. In such instances, the central portion 253 may be pivoted or folded towards the second fluid compartment 222 and the wings 254, 255 may be pivoted or folded downwardly toward the base region 251 of the hanger 250 such that a portion of the elongate member 251 is received within the elongate member receiver 261 (e.g., shown in phantom in FIG. 10). If the user desires that the second fluid compartment 222 and the second cover 284 be directed outwardly, the hanger 250 may be deployed such that the hanger 250 is oriented toward the first fluid compartment 221. The central portion 253 may be pivoted or folded towards the first fluid compartment 221 and the wings 254, 255 may be pivoted or folded downwardly toward the elongate member 251 of the hanger 250 such that a portion of the base region 251 is received within the elongate member receiver 252 (e.g., shown in FIG. 10).

The drainage tube 212 may also be coupled to the patient's drainage site such that drainage fluid can fill the fluid compartments 221, 222. The first cover 281 and/or the second cover 284 may obscure the drainage fluid within the fluid compartments 221, 222. A viewer may observe the volume of drainage fluid within the fluid compartments 221, 222 by viewing the drainage fluid through the first volume indicator 285 and/or the second volume indicator 286. Alternatively, the healthcare worker may observe the volume of drainage fluid within a fluid compartment 221, 222 by lifting a lower portion of the outwardly directed cover 281, 284 and observing the drainage fluid volume through the outwardly directed fluid compartment 221, 222.

Various other types of hangers can also be used in accordance with the fluid assemblies, as shown in FIGS. 11A-11B and 12A-12B. For instance, the hanger 350 of FIGS. 11A-11B does not include a brace receiver or slot. Rather, the hanger is only coupled to the elongate member 351. And in FIGS. 12A-12B, the hanger 450 does not couple to the brace or the elongate member. Other types of hangers can also be used.

Figure 13:
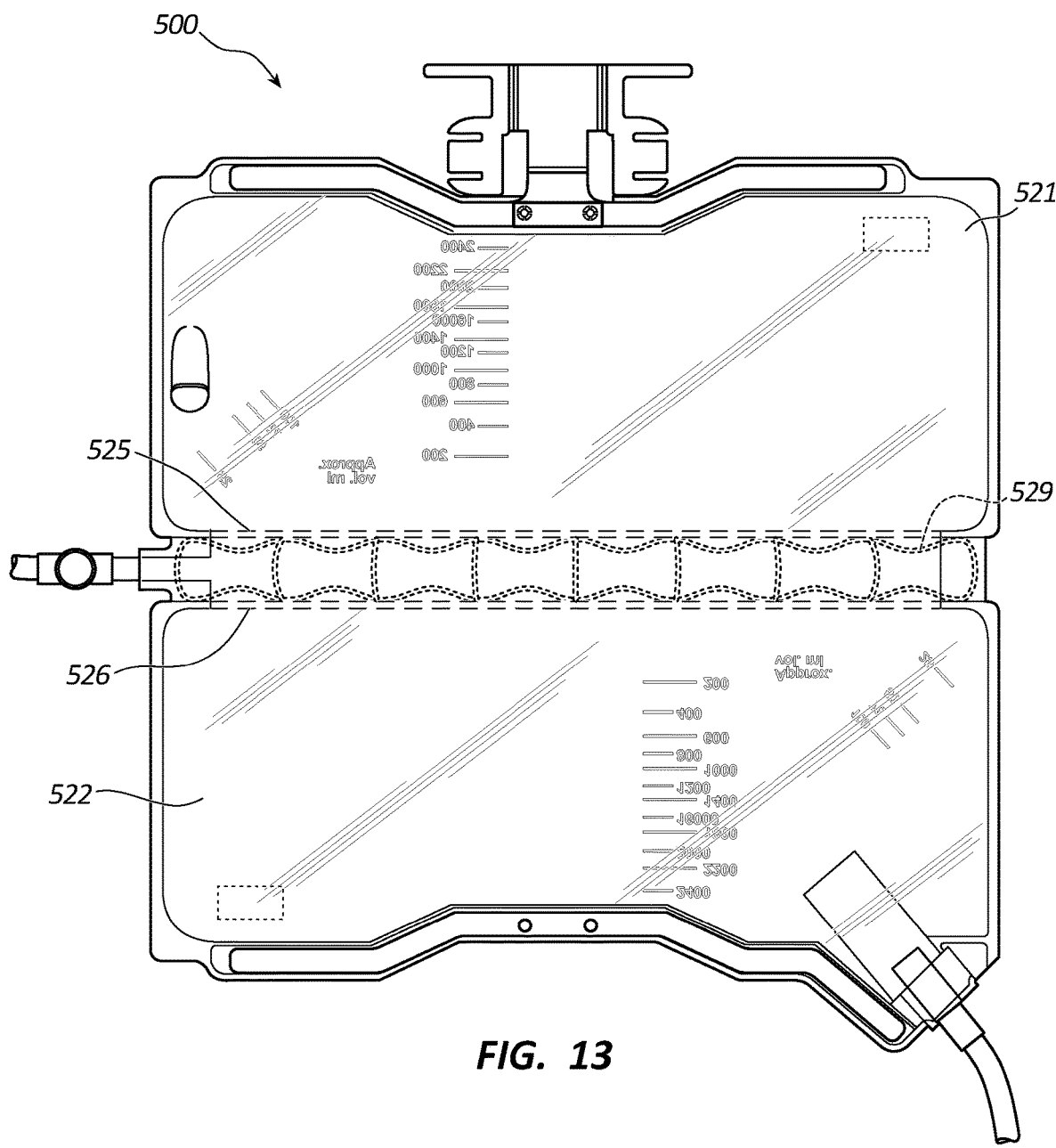
FIG. 13 is plan view of a bodily fluid drainage assembly, depicted in an unassembled configuration.
Figure 14:
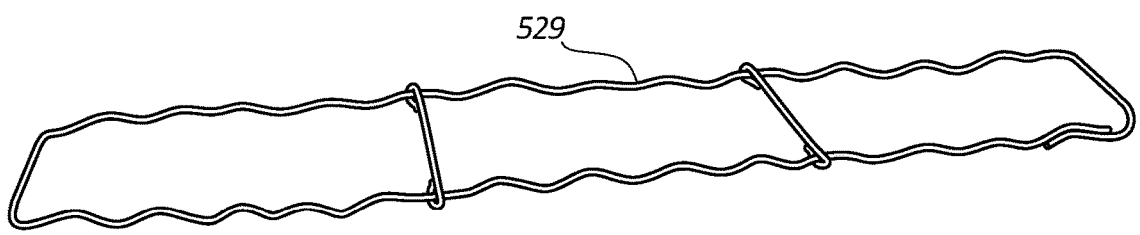
FIG. 14 is a perspective view of a forming structure that can be used with a bodily fluid drainage assembly.

FIG. 13 depicts a bodily fluid drainage assembly 500 in accordance with another embodiment. As shown in FIG. 13, the bodily fluid drainage assembly 500 includes a forming structure 529 that can aid in allowing fluid to flow between the first and second fluid compartments 521, 522. The forming structure 529 can be disposed within the bag structure. For instance, the forming structure 529 can be disposed between the first and second fluid compartments 521, 522 and can be held in place via one or more seams 525, 526. The forming structure 529 can provide a form or shape to a bottom portion of the bag structure (e.g., after it is folded and/or assembled to form first and second fluid compartments 521, 522). The height and/or size of the forming structure can vary as desired. A perspective view of an exemplary forming structure 529 is shown in FIG. 14. Other types and/or shapes and sizes of forming structures can also be used.

Figure 15:
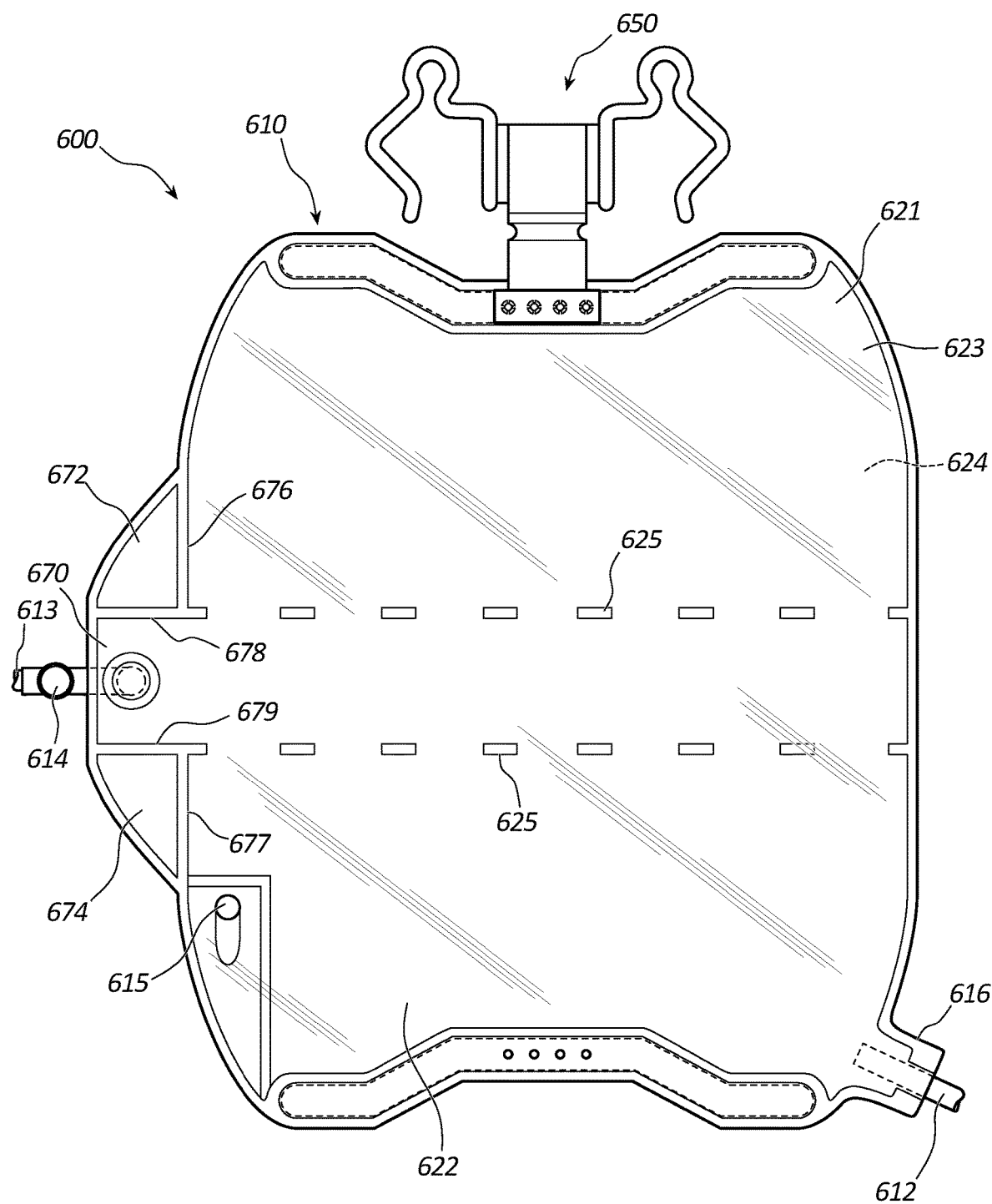
FIG. 15 is a plan view of a bodily fluid drainage assembly, depicted in an unassembled configuration.

FIG. 15 depicts another embodiment of a bodily fluid drainage assembly 600 in an unassembled configuration or state. The bodily fluid drainage assembly 600 includes a drainage bag assembly 610 and a hanger 650. In the embodiment of FIG. 15, the drainage bag assembly 610 includes a first fluid compartment 621 and a second fluid compartment 622. The fluid compartments 621, 622 are in fluid communication with one another, such that fluid from one compartment 621, 622 can flow to and from the other compartment 621, 622. At least one of the fluid compartments 621, 622 comprises an inlet port 616. If desired, at least one of the fluid compartments 621, 622 can comprise an air vent (such as the air vent 117 depicted in FIG. 1).

As shown in FIG. 15, the fluid compartments 621, 622 may comprise a front or first panel 623 and a back or second panel 624, which may be made of one or more liquid impervious materials. For example, the front and back panels 623, 624 may be formed from polyvinyl chloride, polyurethane, vinyl, polymeric, or any other suitable material. At least a portion of the front and back panels 623, 624 can be substantially transparent or translucent such that a drainage fluid contained within the fluid compartments 621, 622 may be readily observed. The panels 623, 624 may be coupled or joined along a peripheral edge thereof via radio frequency (RF) welding, heat sealing, gluing, or any other suitable technique. When coupled together, the panels 623, 624 form a fillable void that may receive drainage fluid via a drainage tube 612 and a corresponding inlet port 616 that are located on an upper portion of at least one of the fluid compartments 621, 622. The panels 623, 624 can also be flexible rather than rigid, such that the fluid compartments 621, 622 can expand as they fill with drainage fluid.

As further shown in FIG. 15, the first and second fluid compartments 621, 622 can be defined by one or more seams 625, 626 that extend across a central region of the drainage bag assembly 610. For instance, the illustrated embodiment includes a first seam 625 and a second seam 626 that are disposed between the first and second fluid compartments 621, 622. The seams 625, 626 can couple one or more regions of the panels 623, 624 together. The seams 625, 626 can also define fold lines or regions where the drainage bag assembly 610 can fold when assembled.

The seams can be made in various ways, such as via radio frequency (RF) welding, heat sealing, gluing, or any other suitable technique. The seams 625, 626 can also be discontinuous, such that they do not block the flow of fluid between the fluid compartments 621, 622. For example, the seams 625, 626 can be referred to as spot seams (or spot welds). In some embodiments, each seam 625, 626 can comprise a series of spot seams (or spot welds). For instance, each seam 625, 626 can comprise three, four, five, six, seven, eight or more spot seams (or spot welds) along a distance of between about 8 and about 16 inches. In particular embodiments, each seam 625, 626 can comprise four, five, or six spot seams (or spot welds) along a distance of between about 8 and about 16 inches. And in more particular embodiments, each seam 625, 626 can comprise five or six spot seams (or spot welds) along a distance of between about 8 and about 16 inches. In some of such embodiments, the drainage bag assembly 610 does not include other conduits (such as conduits 130 in FIG. 1). In such embodiments, fluid can freely flow through the seamed regions 625, 626 and between the first and second fluid compartments 621, 622.

As illustrated, an outlet tube 613 can also be disposed between the fluid compartments 621, 622. The outlet tube 613 may allow the drainage fluid contained within the fluid compartments 621, 622 to be selectively drained from or retained within the fluid compartments 621, 622 via an output regulator 614. The output regulator 614 may comprise a plastic or metal clip, in-line valve, rotatable valve, or any other suitable structure. At least one of the fluid compartments 621, 622 may further comprise an outlet tube holder 615 that comprises a slot, loop, pocket, or hook that is configured to receive and reversibly retain outlet tube 613 in an at least partially upright or folded position. For example, in the illustrated embodiment, the outlet tube holder 615 comprises a plastic tube so as to define a cavity. When the drainage assembly 600 is in a packaged, folded, or filling configuration, a bottom end of the outlet tube 613 can be positioned within the cavity of the outlet tube holder 615.

Figure 18A:
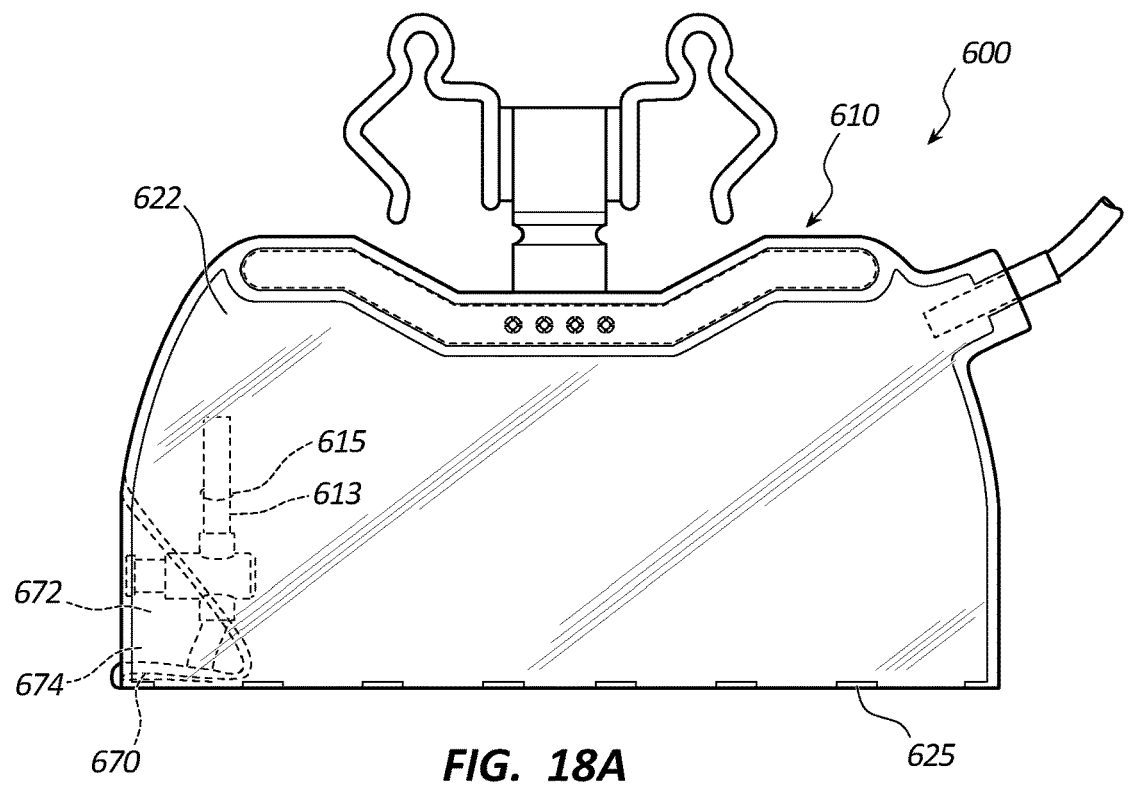
FIG. 18A is a front view of a bodily fluid drainage assembly, depicted with the outlet tube in a folded configuration.
Figure 18B:
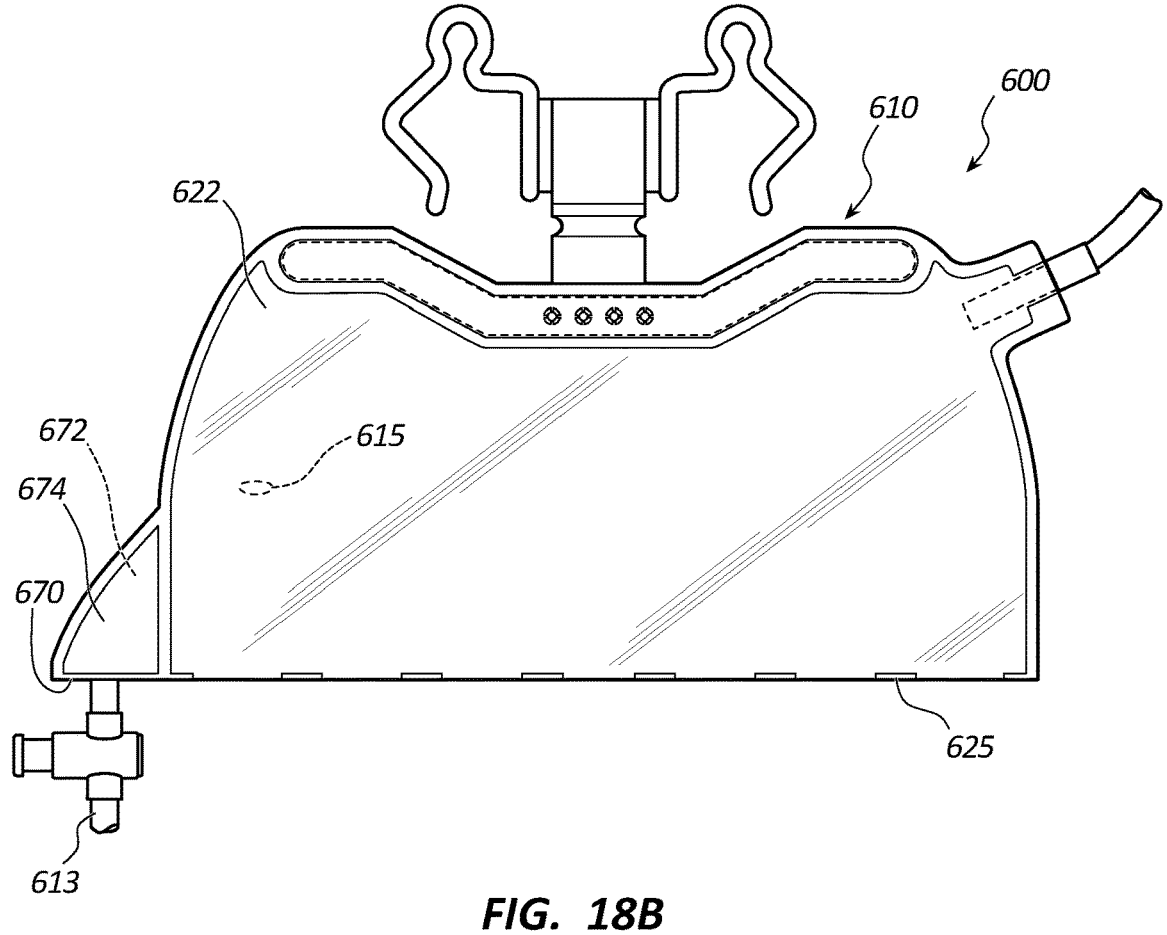
FIG. 18B is a front view of the bodily fluid drainage assembly of FIG. 18A, depicted with the outlet tube in an extended configuration.

The outlet tube 613 can be removed from the outlet tube holder 615 and allowed to hang downwardly into an extended position shown in FIG. 18B during drainage of fluid from the fluid compartments 621, 622.

As further shown in the illustrated embodiment, the fluid compartments 621, 622 can comprise extension members 672, 674 that couple to an extended outlet tube section 670. For example, in FIG. 15 the fluid compartments 621, 622 each comprise an extension member 672, 674 that extends outwardly from the fluid compartment 621, 622. The extension members further couple to the outlet tube section 670 which extends from a central region of the drainage bag assembly 610. The outlet tube section 670 is also coupled to the outlet tube 613 to allow drainage from the drainage bag assembly 610.

In some embodiments, the extension members 672, 674 are integral with the fluid compartments 621, 622. For instance, the extension members 672, 674 can be formed of the same panel material. The extension members 672, 674 can also be defined by one or more seams 676, 677, 678, 679. If desired, the seams 676, 677, 678, 679 can be configured to not allow the passage of fluid. In other embodiments, fluid can be allowed to flow into the extension members 672, 674 and to the outlet tube section 670. When the drainage bag assembly 610 is folded into an assembled state, the extension members 672, 674 can also provide support for the outlet tube section 670. For instance, the extension members 672, 674 can be coupled and configured to retain the outlet tube section 670 in an extended configuration, as further discussed below in relation to FIG. 18B.

Figure 16A:
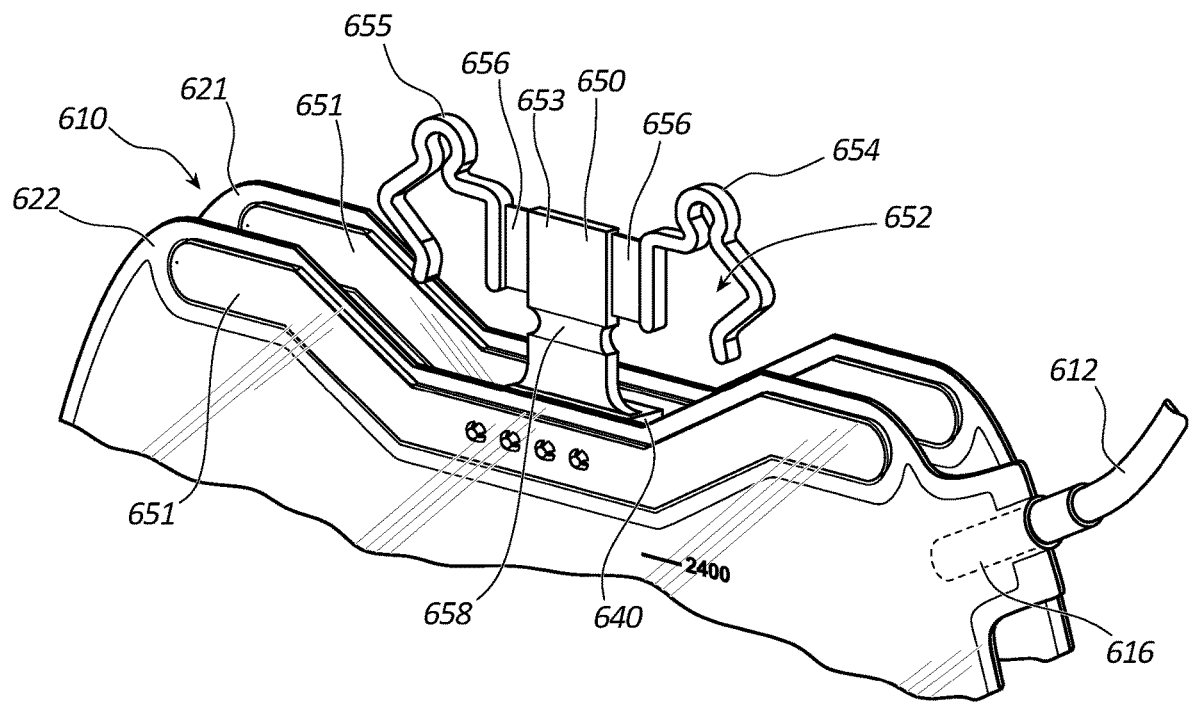
FIG. 16A is a partial view of a bodily fluid drainage assembly, depicted with a hanger in an unfolded state.
Figure 16B:
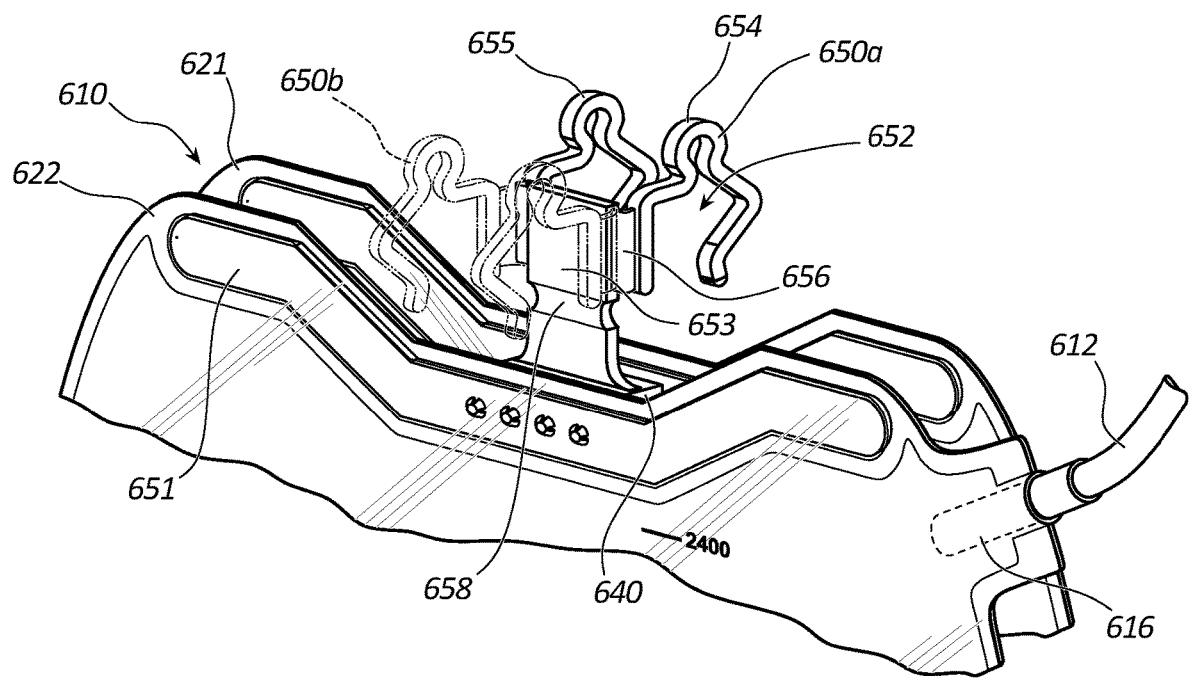
FIG. 16B is a partial view of the bodily fluid drainage assembly of FIG. 16A, depicted with the hanger in a folded state.

FIGS. 16A and 16B depict a portion of the drainage bag assembly 610 in the folded and/or assembled configuration. As shown therein, the drainage bag assembly 610 is folded such that the first fluid compartment 621 and the second fluid compartment 622 are parallel to one another, or side by side. The first fluid compartment 621 is also coupled to the second fluid compartment 622 such that the drainage bag assembly 610 can remain in the folded or assembled configuration during use.

In the illustrated embodiment, the drainage bag assembly 610 includes a base or brace 640 that extends between the first and second fluid compartments 621, 622. For instance, the brace 640 can be coupled to an elongate member 651 of each of the first and second fluid compartments 621, 622 to retain the drainage bag assembly 610 in the assembled configuration. A hanger 650 is also coupled to and extending upward from the base 640.

The hanger 650 can be configured to allow the drainage assembly 600 to be suspended from a patient, or from a support structure, such as a wheelchair, bed, a bed rail, or stand. As shown in FIGS. 16A and 16B, the hanger 650 can be positioned such that it is directed towards either side of the drainage bag assembly 610. For instance, the hanger 650a can be positioned towards the first fluid compartment 621, or the hanger 650b can be positioned towards the second fluid compartment 622, as desired by the practitioner (e.g., a practitioner may suspend the drainage assembly 600 in either direction, depending on a desired orientation of the inlet port 616 and tube 612). The hanger 650 may be formed as an integral unit using any suitable manufacturing technique, such as injection molding, casting, machining, etc. In other embodiments, the hanger 650 may be assembled from separate components using any suitable assembly technique. The hanger 650 may be formed from any suitable material, such as a polymeric material like polypropylene, polyethylene, blends thereof, etc.

As further illustrated in FIGS. 16A-16B, the hanger 650 may include a central portion 653, a first extending member or arm 654, and a second extending member or arm 655. The central portion 653 may be coupled to the brace 640 and may also include a flexible or living hinge 658 such that a face of the central portion 653 can be configured to flex and/or bend towards the first and second fluid compartment 621, 622 if desired. For instance, the hanger 650 can be bent towards either the first or second fluid compartment 621, 622 during packaging and/or shipping. The hanger 650 can also be bent towards either the first or second fluid compartment 621, 622 when being suspended from an object.

The first and second arms 654, 655 can also be coupled to the central portion 653 via a flexible or living hinge 656 such that the arms 654, 655 are oriented in a plane of the face of the central portion 653 in the undeployed state, as shown in FIG. 16A. The living hinge 656 may allow the arms 654, 655 to pivot or fold about the living hinge 656 approximately or at least 180 degrees relative to the plane of the face of the central portion 653 (e.g., at least 90 degrees in either direction). In other words, the arms 654, 655 may be pivoted from the parallel orientation to a perpendicular orientation on either side of the central portion 653 when the hanger 650 is deployed, as depicted in FIG. 16B. The arms 654, 655 may include a support receiver 652 configured to be clipped over or disposed over a portion of a hospital bed rail. In other embodiments, the support receiver 652 may be configured to be clipped over or disposed over any suitable support, such as a wheelchair, a stand, etc.

Figure 24A:
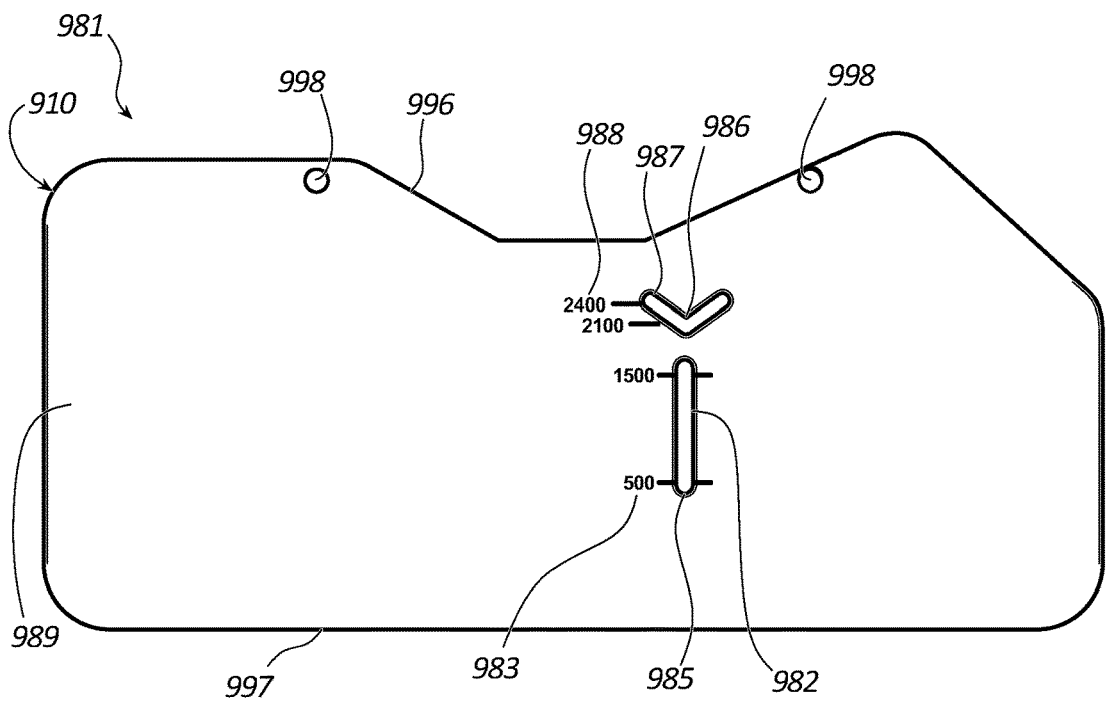
FIG. 24A is a front view of a cover of a bodily fluid drainage assembly.

Although not depicted in FIGS. 16A and 16B, it will be appreciated that the drainage bag assembly 610 can further include one more covers (similar to covers 281, 284 shown in FIG. 7 or cover 981 shown in FIG. 24A). The drainage bag assembly 610 can further include one or more other features previously discussed, such as one or more graduations (like graduations 134, 135 shown in FIGS. 5A-5C), etc.

Figure 17:
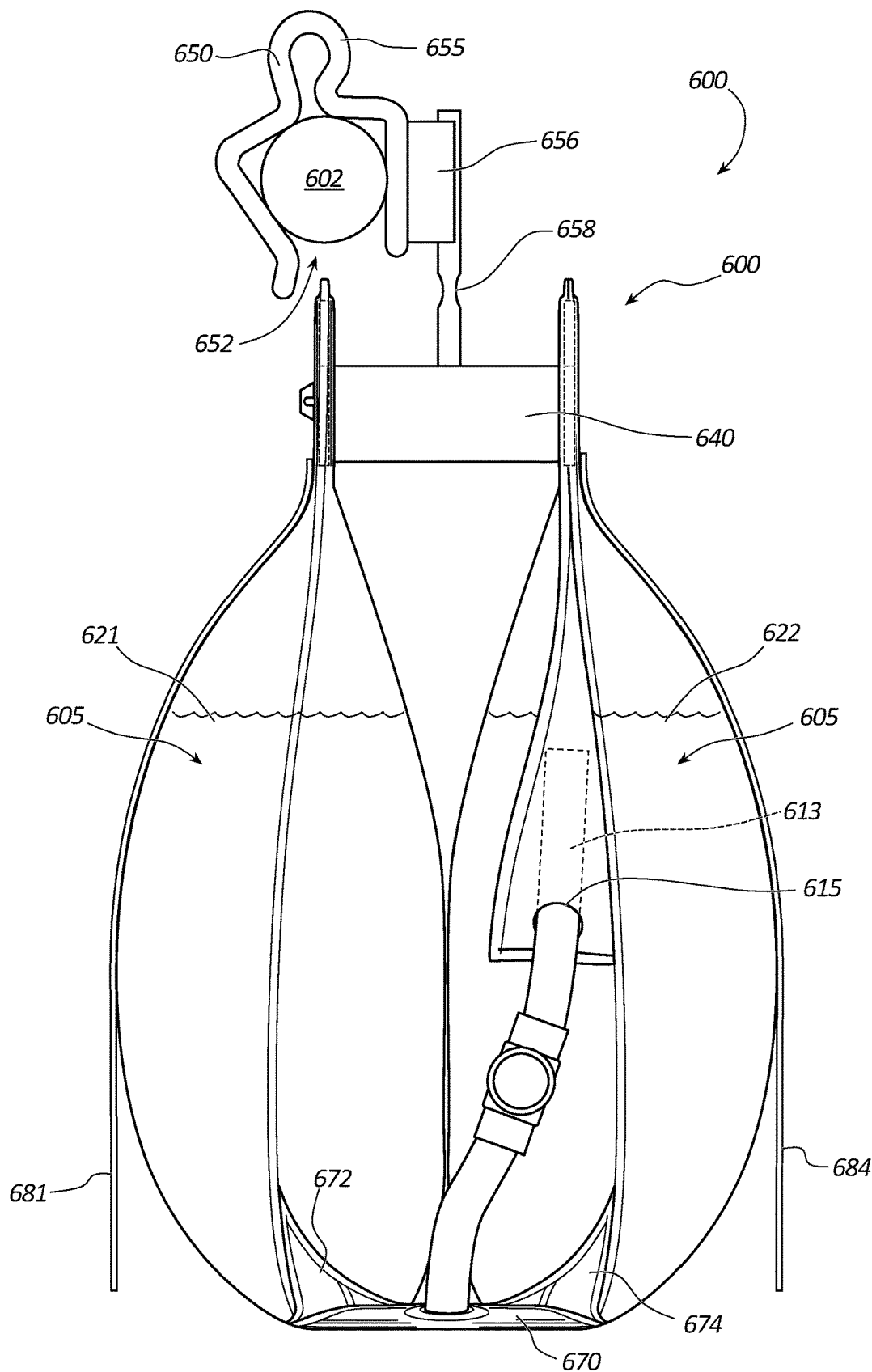
FIG. 17 is an end view of a bodily fluid drainage assembly.

FIG. 17 depicts an end view of a drainage assembly 600 that includes first and second fluid compartments 621, 622 each having a cover 681, 684 coupled thereto. As shown in FIG. 17, the covers 681, 684 can couple to an upper region of the first and second fluid compartments 621, 622, and drape downwardly over the outwardly facing surfaces of the fluid compartments 621, 622. In such a manner, fluid 605 within the fluid compartments 621, 622 can be obscured from view by an observer. As previously discussed, a bottom portion of each cover 681, 684 can also be lifted as desired to view the fluid 605 within the fluid compartments 621, 622.

FIG. 17 also depicts a hanger 650 extending from a base 640 that couples the fluid compartments 621, 622 together. As shown in FIG. 17, the hanger 650 is configured to couple to a rail 602 or other structure. In the illustrated embodiment, the hanger 650 is depicted in a folded configuration or state, wherein each arm 654, 655 is pivoted or folded about a hinge 656 towards the first fluid compartment 621. The support receiver 652 is also shown disposed over a rail 602. If desired, the arms 654, 655 could also pivot or fold towards the second fluid compartment 622 (e.g., in instances where the rail is on the other side of the drainage bag assembly 610). The hanger 650 can also pivot or fold about hinge 658 if required.

As further shown in FIG. 17, the fluid 605 height is substantially the same in each of the first and second fluid compartments 621, 622 as the fluid can flow freely between the fluid compartments 621, 622. Prior to draining fluid 605 from the drainage bag assembly 610, the extension members 672, 674 and outlet tube section 670 are folded inwards towards the drainage bag assembly 610 and the outlet tube 613 is disposed in or housed within the outlet tube holder 615.

FIGS. 18A and 18B depict the drainage assembly 600 in a folded or assembled configuration during use. Specifically, FIG. 18A depicts the drainage assembly 600 with the outlet tube 613 in a folded configuration, and FIG. 18B depicts the drainage assembly 600 with the outlet tube 613 in an extended configuration. When folded, the fluid compartment 622 is defined at a bottom end by seam 625. The drainage bag assembly 610 is also shown without covers 681, 684 for ease of reference, but it is understood that one or more covers 681, 684 could be coupled to the drainage assembly 600 if desired.

With reference to FIG. 18A, the outlet tube 613 can be disposed in an upright or folded configuration prior to draining fluid from the drainage bag assembly 610. For instance, the outlet tube 613 can be disposed in the folded configuration while the drainage bag assembly 610 is being filled with fluid. In the folded configuration, the outlet tube is positioned or housed within the outlet tube holder 615. The extension members 672, 674 are also folded inwardly towards the drainage bag assembly 610.

When a practitioner desires to empty or drain fluid from the drainage bag assembly 610, the outlet tube 613 can be transitioned to an extended or drainage configuration, as shown in FIG. 18B. When transitioning to the extended configuration, the outlet tube 613 is removed from the outlet tube holder 615, pulled outwards away from the drainage bag assembly 610, and pivoted downwards (e.g., between about 150-200 degrees, or about 180 degrees). In doing so, the outlet tube section 670 is also pivoted from a first position disposed inwards towards the drainage bag assembly 610 to a second position disposed outwards and extending from the drainage bag assembly 610. In the extended or drainage configuration, the outlet tube 613 is also directed downwards for drainage.

When transitioning to the extended configuration, the extension members 672, 674 are also inverted and folded from a first position disposed inwards towards the drainage bag assembly 610 to a second position disposed outwards and extending from the drainage bag assembly 610. In the extended position, the extension members 672, 674 can support the outlet tube section 670 to help retain the outlet tube 613 in the downward orientation. The extension members 672, 674 can also aid in keeping the outlet tube section 670 from kinking or bending which can restrict flow to the outlet tube 613.

After a practitioner empties or drains fluid from the drainage bag assembly 610, the practitioner can transition the outlet tube 613 back to the folded configuration. It will thus be appreciated that the outlet tube 613 can be transitioned between the folded configuration of FIG. 18A and the extended configuration of FIG. 18B as desired.

Figure 19:
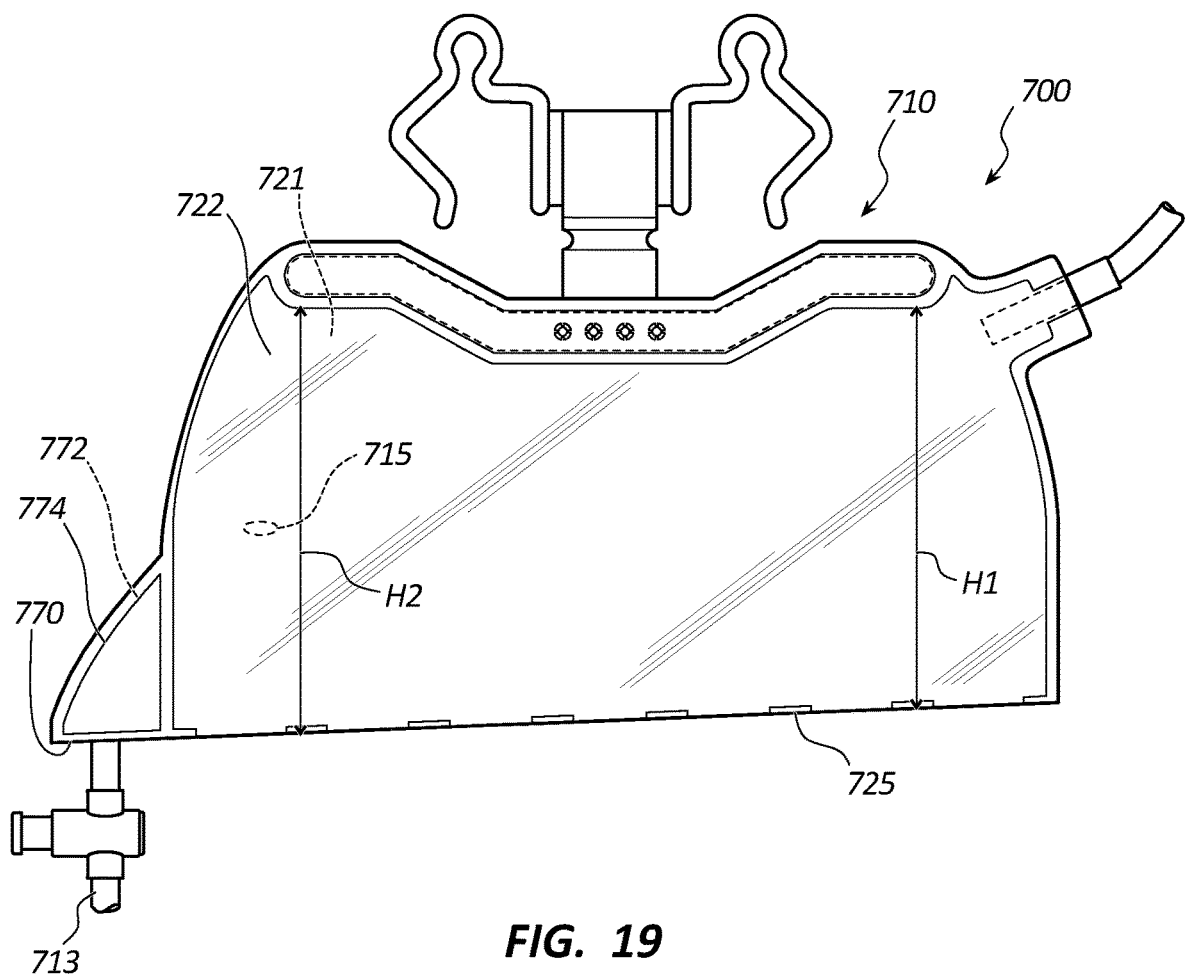
FIG. 19 is a front view of another bodily fluid drainage assembly, depicted with the outlet tube in an extended configuration.

FIG. 19 depicts a drainage assembly 700 according to yet another embodiment. In FIG. 19, the bottom section of the drainage bag assembly 710 is configured to angle and/or slope towards the outlet tube section 770 and outlet tube 713. For instance, each fluid compartment 721 can be configured such that the seam 725 defines an angle or slope when the drainage bag assembly 710 is folded and assembled for use. As shown in FIG. 19, the height H2 on the first side or end of the fluid compartment 722 is greater than the height H1 on the second side or end such that the bottom end of the fluid compartment 722 is not parallel with the top end. Configuring the fluid compartments 721, 722 with a bottom that slopes and angles towards the extension members 772, 774 and outlet tube section 770 can aid in directing the flow of fluid towards the outlet tube 713 for optimal drainage and emptying of the drainage bag assembly 710.

Figure 20A:
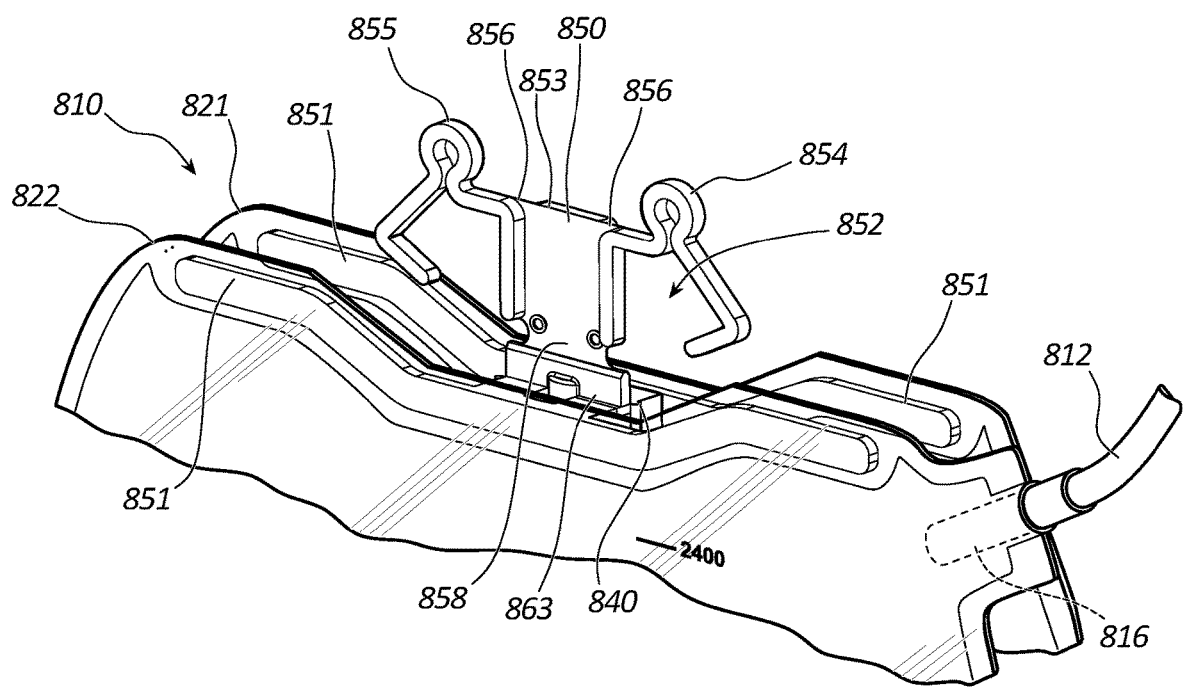
FIG. 20A is a partial view of a bodily fluid drainage assembly, depicted with a hanger in an unfolded state.

FIGS. 20A-23B depict another embodiment of a drainage bag assembly 810. FIGS. 20A and 20B depict a portion of the drainage bag assembly 810 in the folded and/or assembled configuration. As shown therein, the drainage bag assembly 810 is folded such that the first fluid compartment 821 and the second fluid compartment 822 are parallel to one another, or side by side. The first fluid compartment 821 is also coupled to the second fluid compartment 822 such that the drainage bag assembly 810 can remain in the folded or assembled configuration during use.

Figure 20B:
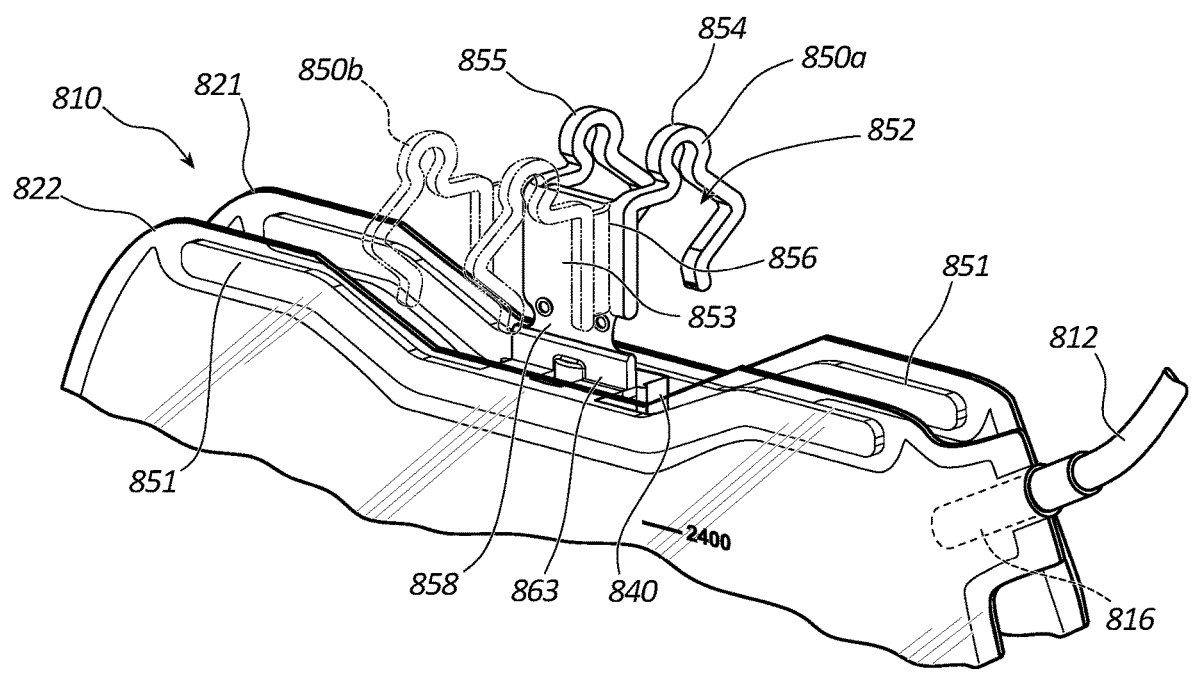
FIG. 20B is a partial view of the bodily fluid drainage assembly of FIG. 20A, depicted with the hanger in a folded state.
Figure 21:
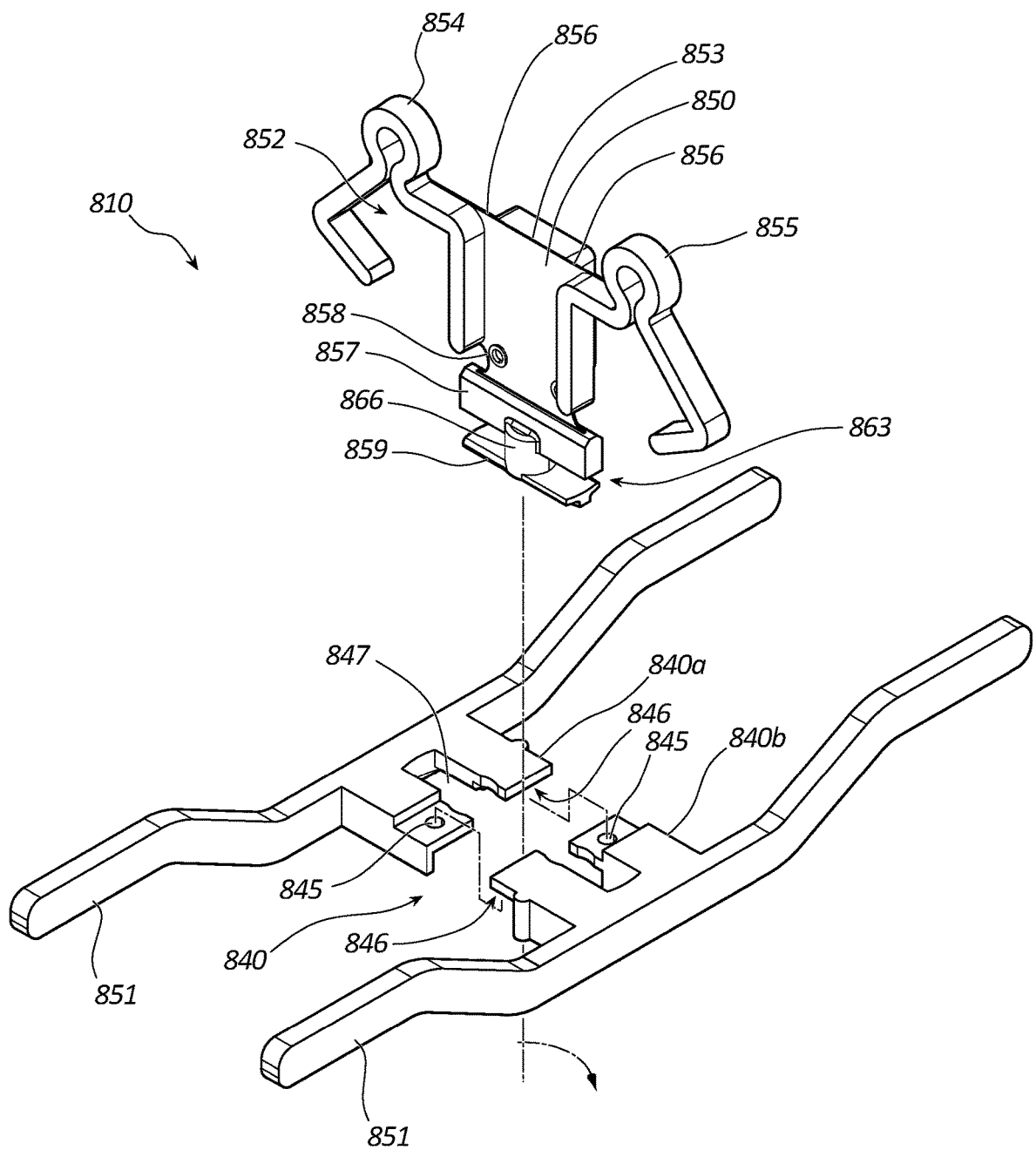
FIG. 21 is an exploded perspective view of the hanger and a base of the bodily fluid drainage assembly of FIG. 20A.

In the illustrated embodiment of FIG. 20A-21, the drainage bag assembly 810 includes a base or brace 840 that extends between the elongate members 851. The base 840 may include a first base portion 840a coupled to and extending laterally from one elongate member 851 and a second base portion 840b coupled to and extending laterally from another elongate member 851. The first base portion 840a and the second base portion 840b may be configured to fixedly couple together. For instance, the first and second base portions 840a, 840b may include passages 845 that engage with pins or protrusions 846 when the first and second base portions 840a, 840b are coupled together. Other coupling configurations, such as snap fit, adhesive, loop and hook, etc., are also contemplated within the scope of the disclosure. In some embodiments, the first and second base portions 840a, 840b may be configured to releasably couple together. The base 840 may further include a slot 847 configured for coupling of a hanger 850 to the base 840.

The hanger 850 may be coupled to and extend upward from the base 840. The hanger 850 can be configured to allow the drainage bag assembly 810 to be suspended from a patient, or from a support structure, such as a wheelchair, bed, a bed rail, or stand. As shown in FIG. 20B, the hanger 850 can be positioned such that it is directed towards either side of the drainage bag assembly 810. For instance, the hanger 850a can be positioned towards the first fluid compartment 821, or the hanger 850b can be positioned towards the second fluid compartment 822, as desired by the practitioner (e.g., a practitioner may suspend the drainage bag assembly 810 in either direction, depending on a desired orientation of the inlet port 816 and tube 812). The hanger 850 may be formed from any suitable material, such as a polymeric material like polypropylene, polyethylene, blends thereof, etc.

As further illustrated in FIGS. 20A-21, the hanger 850 may include a central portion 853, a first extending member or arm 854, a second extending member or arm 855, and a base coupler 863. The central portion 853 may be coupled to the base 840 and may also include a flexible or living hinge 858 such that a face of the central portion 853 can be configured to flex and/or bend towards the first and/or second fluid compartment 821, 822 if desired. For instance, the hanger 850 can be bent towards either the first or second fluid compartment 821, 822 during packaging and/or shipping. The hanger 850 can also be bent towards either the first or second fluid compartment 821, 822 when being suspended from an object.

The first and second arms 854, 855 can also be coupled to the central portion 853 via a flexible or living hinge 856 such that the arms 854, 855 are oriented in a plane of the face of the central portion 853 in the undeployed state, as shown in FIG. 20A. The living hinge 856 may allow the arms 854, 855 to pivot or fold about the living hinge 856 approximately or at least 180 degrees relative to the plane of the face of the central portion 853 (e.g., at least 90 degrees in either direction). In other words, the arms 854, 855 may be pivoted from the parallel orientation to a perpendicular orientation on either side of the central portion 853 when the hanger 850 is deployed, as depicted in FIG. 20B. The arms 854, 855 may also include a support receiver 852 configured to be clipped over or disposed over a portion of a support structure (e.g., like a hospital bed rail).

Figure 22A:
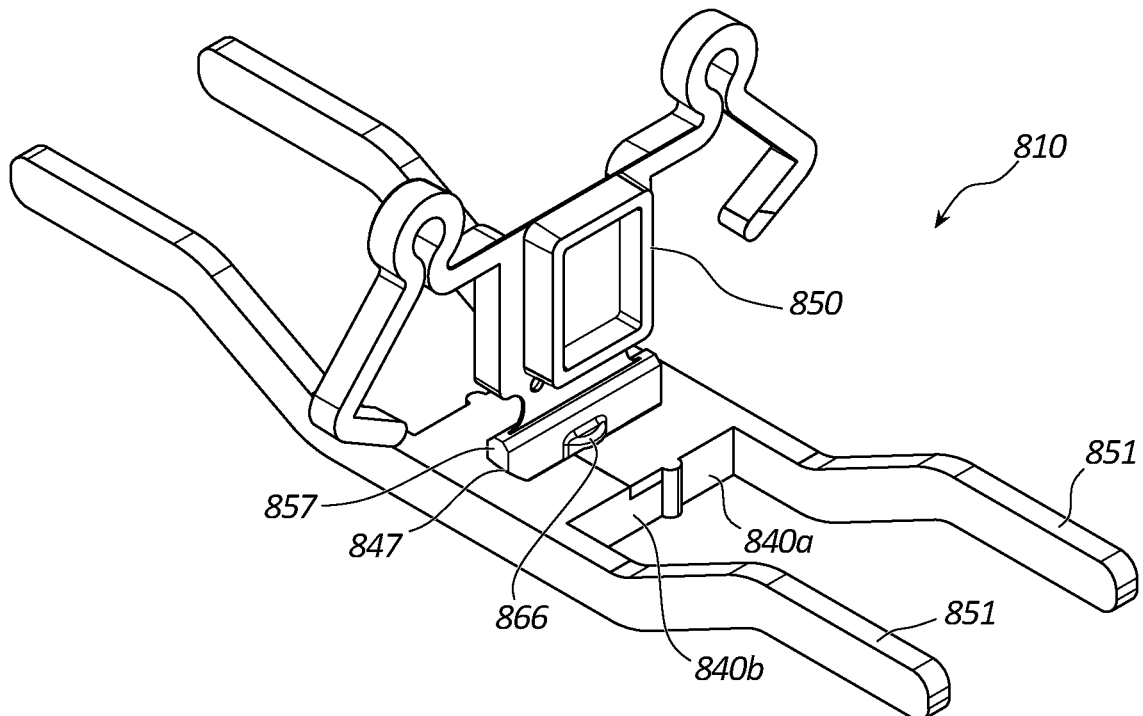
FIG. 22A is a top perspective view of the hanger and base of the bodily fluid drainage assembly of FIG. 20A, depicted in a pre-locked configuration.
Figure 22B:
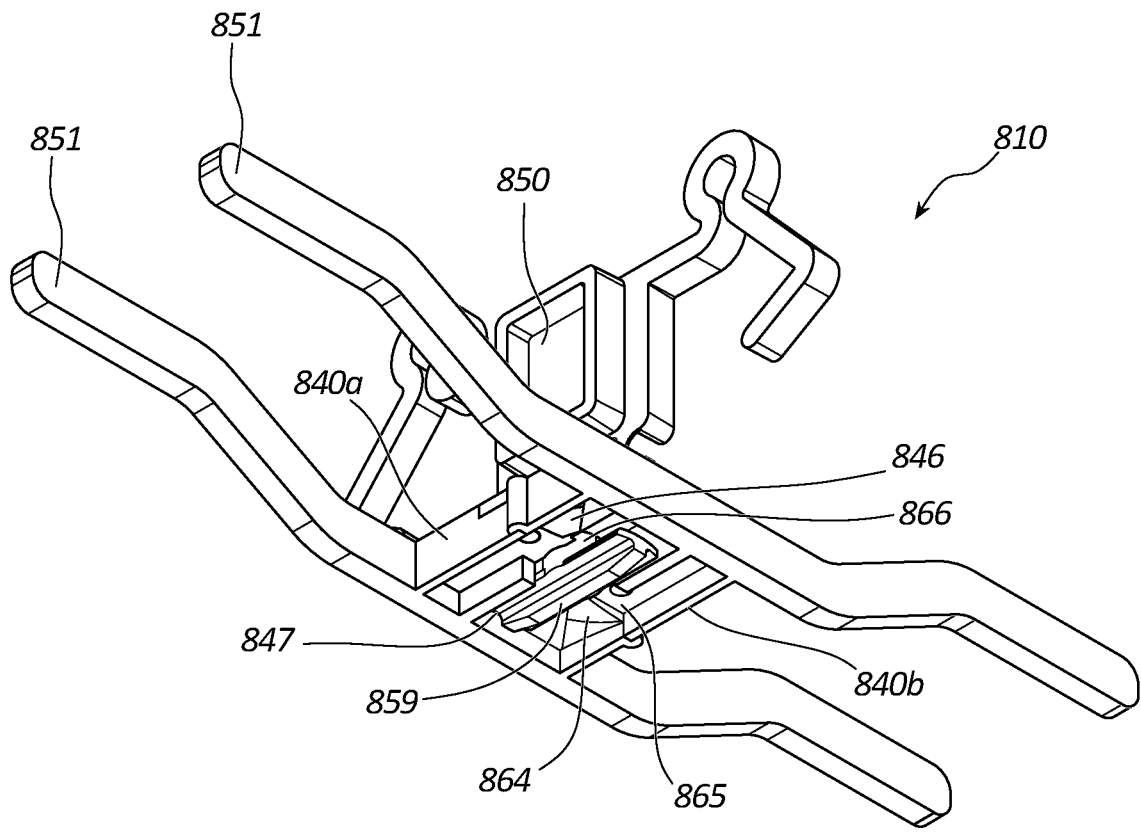
FIG. 22B is a bottom perspective view of the hanger and base of the bodily fluid drainage assembly of FIG. 20A, depicted in the pre-locked configuration.

The hanger 850 may be coupled to the base 840 using any suitable assembly technique. For instance, as depicted in FIGS. 21-23B, the base coupler 863 of the hanger 850 can be disposed within the slot 847 of the base 840 such that a cylindrical central portion 866 is disposed within the slot 847, an upper portion 857 is disposed above the slot 847, and a lower portion 859 is disposed below the slot 847. As depicted in FIGS. 22A and 22B, the hanger 850 is oriented perpendicular to a longitudinal axis of the elongate members 851 in a pre-locked configuration. As shown in FIG. 22B, the lower portion 859 is positioned at a base of ramps 864 which are disposed on a bottom surface of the first and second base portions 840a, 840b. The ramps 864 are inclined downwardly away from the bottom surface and define a channel 865.

Figure 23A:
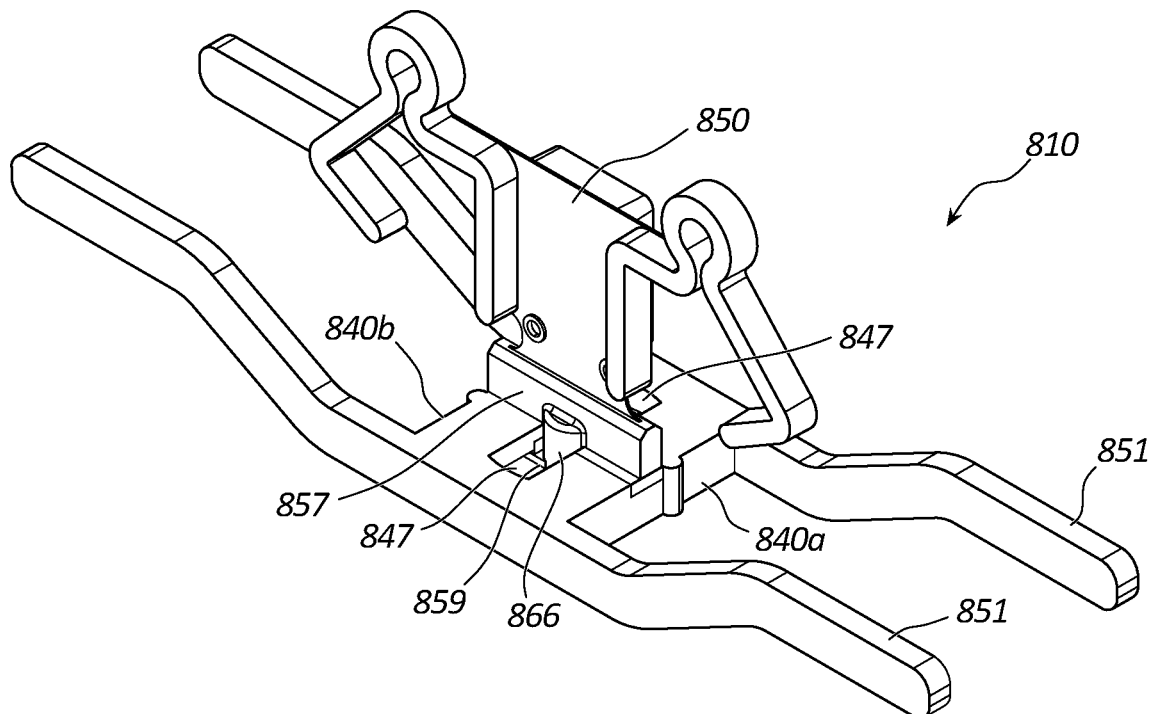
FIG. 23A is a top perspective view of the hanger and base of the bodily fluid drainage assembly of FIG. 20A, depicted in a locked configuration.
Figure 23B:
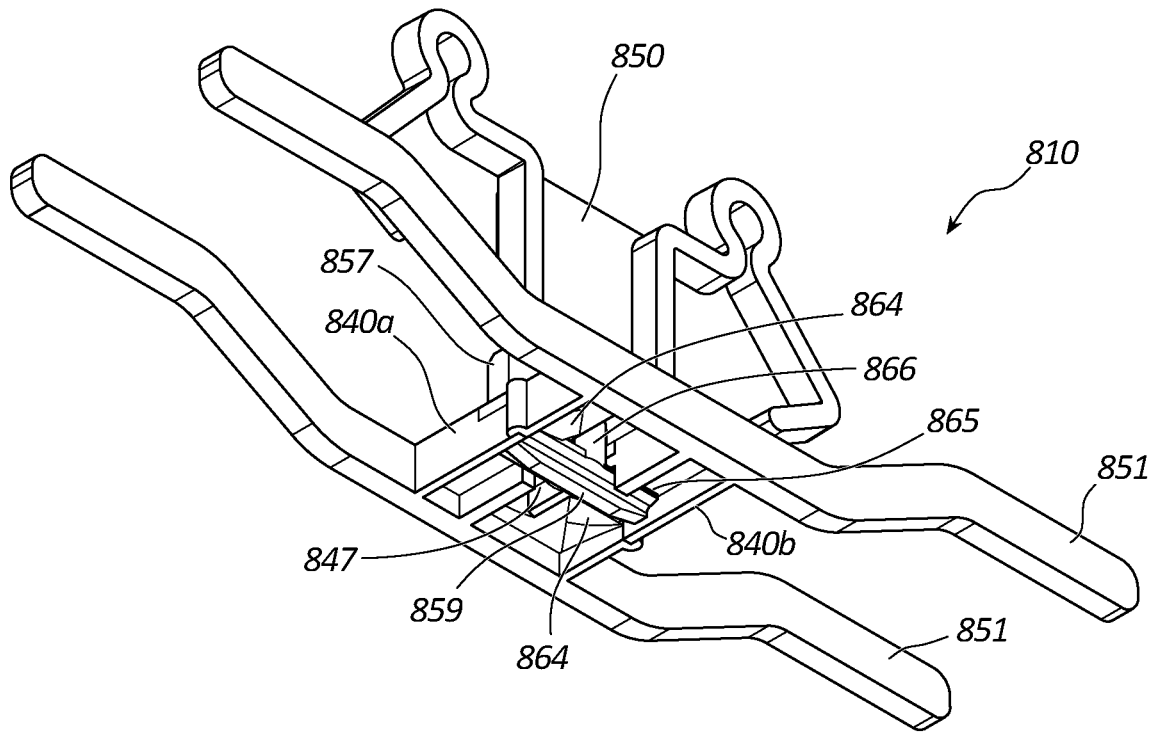
FIG. 23B is a bottom perspective view of the hanger and base of the bodily fluid drainage assembly of FIG. 20A, depicted in the locked configuration.

FIGS. 23A-23B illustrate the hanger 850 in a locked configuration. In the locked configuration, the hanger has been rotated 90 degrees in a first direction from the pre-locked configuration such that it is oriented parallel to the longitudinal axis of the elongate members 851. During rotation, the lower portion 859 engages with the ramps 864 and is turned such that it moves to a position where it is disposed within the channel 865 at the end of the rotation. The channel 865 is disposed between the ramps 864 and is configured to restrict rotation of the hanger 850 in a second direction to decouple the hanger 850 from the base portions 840a, 840b. For instance, the ramps 864 can include shoulders that restrict rotation of the hanger 850 in the second or reverse direction. When in the locked configuration, the base portions 840a, 840b can also be locked in their engaged position such that they cannot be separated or otherwise pulled apart. The bag assembly 810 can thus remain in the assembled or folded configuration for use. In other embodiments, the hanger 850 can be rotated in a reverse direction (after being locked or engaged) by applying a sufficient force such that the hanger 850 can optionally be removed from the channel 865, and the base portions 840a, 840b can be optionally separated.

Although not depicted in FIGS. 20A and 20B, it will be appreciated that the drainage bag assembly 810 can further include one more covers (similar to covers 281, 284 shown in FIG. 7 or cover 981 shown in FIG. 24A). The drainage bag assembly 810 can further include one or more other features previously discussed, such as one or more graduations (like graduations 134, 135 shown in FIGS. 5A-5C), etc.

Figure 24B:
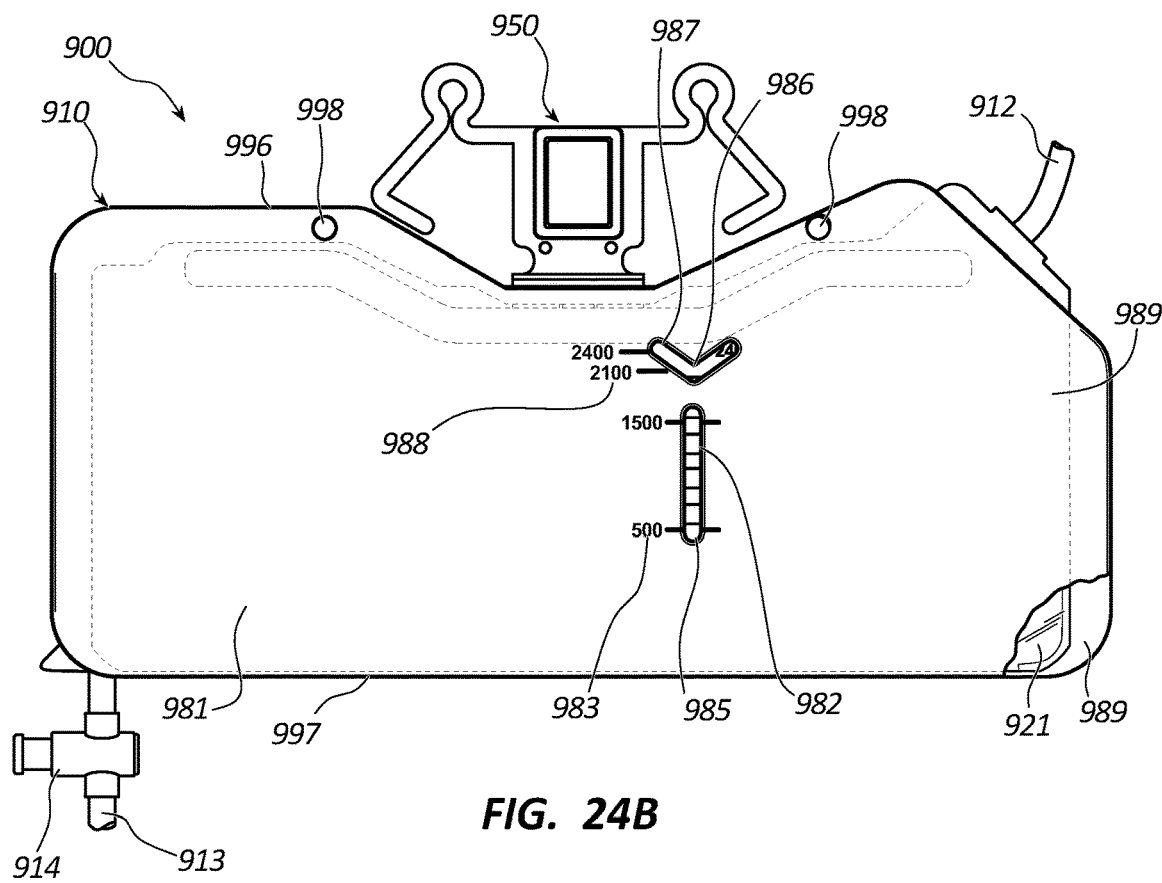
FIG. 24B is a front view of another bodily fluid drainage assembly including the cover of FIG. 24A in an obscuring orientation.

As shown in FIGS. 24A and 24B, in certain embodiments, a bodily fluid drainage assembly 900 can include a drainage bag assembly 910 comprising a cover 981 that can be formed from or otherwise include an opaque material (or at least partially opaque material capable of obscuring the appearance of a fluid within the drainage bag assembly 910 when in use), and that may define a sleeve to selectively cover portions of the drainage bag assembly 910. For example, the cover 981 may be formed from polyvinyl chloride, polyurethane, vinyl, polymeric, or any other suitable material. The cover 981 may comprise front and back panels 989 that define a cavity configured to receive the drainage bag assembly 910. Side ends or edges of the panels 989 may be welded together and lower ends or edges of the panels 989 may be uncoupled defining a lower opening 997 to the cavity. Upper ends or edges of the panels 989 may define an upper opening 996 and may include one or more fasteners 998 configured to selectively couple the upper ends together to close the upper opening 996. The fasteners 998 may be of any suitable type, such as snaps, clips, hook-and-loop, zippers, buttons, etc. As depicted in FIG. 24B, the cover 981 is located adjacent to and is configured to obscure a fluid compartment 921.

The cover 981 can include one or more volume indicators 985. The illustrated first volume indicator 985 includes a window 982 and one or more graduations 983. A variety of configurations for the window 982 and the graduations 983 are possible. For example, a variety of shapes are possible for the window 982, and the number and arrangement of the graduations 983 may be varied. In the illustrated embodiment, the window 982 defines a permanent opening through the cover 981 and is fully encompassed by solid or unbroken portions of the cover 981. The window 982 defines a small, vertically oriented longitudinal slot. Only a small portion of the fluid compartment 921 is visible through the window 982 when the cover 981 is in an obscuring orientation. An approximate volume level can be determined when a top level of the drainage fluid is visible through the window 982, such as by comparing the level of the drainage fluid to the graduations 983. Due to the fixed relationship between the upper end of the cover 981 and the fluid compartment 921, the graduations 983 can provide a substantially accurate assessment of the approximate liquid volume when the cover 981 is in the obscuring orientation.

The cover 981 may include a second volume indicator 986. The second volume indicator 986 includes a recess, such as a notch or cutout 987, and a set of graduations 988. A bottom end of the cutout 987 is at a position that is horizontally offset and/or spaced vertically from an upper end of the window 982. Due to the difference in vertical positions between the cutout 987 and the window 982, a top level of the drainage fluid can remain below the cutout 987 at all times that the window 982 is used in determining the approximate volume of the drainage fluid, and the top level of the drainage fluid can remain above the window 982 at all times that the cutout 987 is used in determining the approximate volume of the drainage fluid. In some embodiments, the cover 981 may include volume indicators similar to first and second volume indicators 985, 986 disposed on both the front and back panels 989 configured to determine the approximate volume of the drainage fluid within first and second drainage bags.

In FIG. 24B, the cover 981 is shown in the obscuring orientation. In other words, the cover 981 is shown disposed over the drainage bag assembly 910 and obscuring at least a portion of the fluid compartment 921. The cover 981 may be disposed in the obscuring orientation by unfastening the fasteners 998 to open the upper opening 996 of the cover 981 and sliding the drainage bag assembly 910 into the cavity of the cover 981 such that a hanger 950 extends at least partially through the upper opening 996 and an output regulator 914 and an output tube 913 extends at least partially through the lower opening 997. The hanger 950 may be similar to any of the previously disclosed hangers of the present disclosure. Alternatively, the drainage bag assembly 910 may be slid into the cavity through the lower opening 997 of the cover 981. When the cover 981 is in the obscuring orientation, the fasteners 998 may be closed to close the upper opening 996 and secure the cover 981 in the obscuring orientation. To transition the cover 981 to a viewing orientation, a portion of the cover 981 may be displaced upwardly (e.g., from the bottom edge such as by the drainage tube 912) to reveal at least a lower portion of the fluid compartment 921. Alternatively, the fasteners 998 may be opened to open the upper opening 996 and a portion of the cover 981 may be displaced downwardly to reveal at least an upper portion of the fluid compartment 921.

Figure 25:
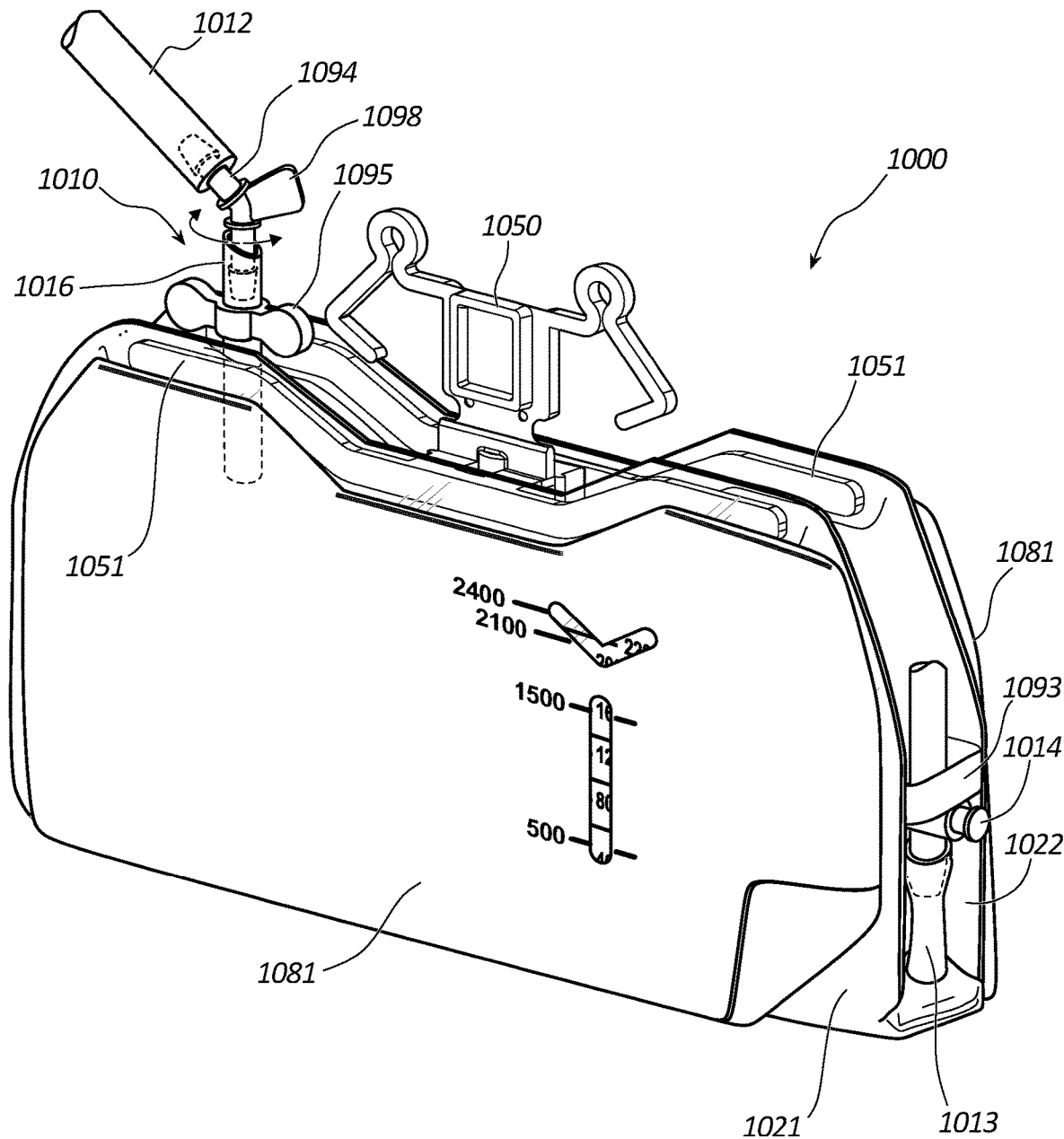
FIG. 25 is a perspective view of another embodiment of a bodily fluid drainage assembly including a rotatable elbow connector.

As shown in FIG. 25, in certain embodiments, a bodily fluid drainage assembly 1000 can include a drainage bag assembly 1010 comprising a cover 1081 that can be formed from or otherwise include an opaque material (or at least partially opaque material capable of obscuring the appearance of a fluid within the drainage bag assembly 1010 when in use). For example, the cover 1081 may be formed from polyvinyl chloride, polyurethane, vinyl, polymeric, or any other suitable material. The cover 981 may comprise front and back panels that can obscure fluid compartments 1021, 1022 when in use. The front and back panels of the cover 1081 may be configured to obscure substantially all of the fluid compartments 1021, 1022. As depicted in FIG. 25, a top edge of the front panel of the cover 1081 is coupled (e.g., welded) to a top edge of the front fluid compartment 1021. The weld extends substantially across a width of the fluid compartment 1021 such that the cover 1081 obscures the fluid compartment 1021 from top to bottom and from side to side. In other words, the cover 1081 is coupled to the fluid compartment 1021 adjacent an elongate member 1051 of the hanger 1050. In some embodiments, the weld may follow a contour of the elongate member 1051. The fluid compartment 1022 and back panel of the cover 1081 can be configured likewise.

The illustrated embodiment of FIG. 25 depicts an inlet port 1016 in fluid communication with the fluid compartment 1022 of the drainage bag assembly 1010. Alternatively, the fluid port 1016 may be in fluid communication with the fluid compartment 1021. An elbow connector 1094 is rotationally coupled to and extends upward from the inlet port 1016 at one end and is fluidly coupled to a drainage tube 1012 at an opposite end. The elbow connector 1094 is configured to be rotated relative to the inlet port 1016 to facilitate redirecting the drainage tube 1012 (e.g., such that the drainage tube 1012 can be oriented at any direction in relation to the assembly 1010). The elbow connector 1094 can include a fixed angle bend ranging from about 30 degrees to about 60 degrees, from about 40 degrees to about 50 degrees, and can be about 45 degrees relative to a vertical axis of the elbow connector 1094. In other embodiments, the elbow connector 1094 may include a swivel joint disposed at the bend of the elbow connector 1094. The swivel joint may allow the angle of the elbow connector 1094 to be adjustable from about zero degrees to about 90 degrees, from about 30 degrees to about 60 degrees, and from about 40 degrees to about 50 degrees relative to the vertical axis of the elbow connector 1094.

A rotation tab or wing 1098 may be coupled to the elbow connector 1094. The rotation tab 1098 may extend outwardly from the vertical axis and be disposed adjacent the bend of the elbow connector 1094. The user may grasp the rotation tab 1098 to rotate the elbow connector 1094 to change an orientation of the drainage tube 1012. In other embodiments, the elbow connector 1094 may not include the rotation tab 1098 and the elbow connector 1094 may be rotated by grasping a body of the elbow connector 1094. An anti-rotation handle 1095 may also optionally be fixedly coupled to an upper portion of the inlet port 1016. The anti-rotation handle 1095 may include at least one lateral extension configured to be gripped by a user to rotationally secure the inlet port 1016 relative to the fluid compartment 1022. When grasped by a user, the anti-rotation handle 1095 can prevent rotation of the inlet port 1016 as the elbow connector 1094 is rotated. If the inlet port 1016 is rotated, the material of the fluid compartment 1022 may tear or rip and compromise the fluid integrity of the fluid compartment 1022. The anti-rotation handle 1095 may be used in cooperation with the rotation tab 1098 to rotate the elbow connector 1094 to re-orient the drainage tube 1012 without compromising the fluid integrity of the fluid compartment 1022. In other embodiments, no anti-rotation handle 1095 is used.

FIG. 25 illustrates the drainage bag assembly 1010 including a retention band 1093. The band 1093 may be fixedly or releasably coupled to side edges of the fluid compartments 1021, 1022. The band 1093 may be formed from the same material used to form the fluid compartments 1021, 1022, or a different material. The band 1093 may be about one inch wide and have a length that accommodates expansion of the fluid compartments 1021, 1022 when filled with fluid. The band 1093 may be configured to retain an outlet port 1013 in an upward vertical orientation when the fluid compartments 1021, 1022 are not being drained. A distal portion of an output regulator 1014 may be selectively disposed inside of the band 1093 to retain the outlet port 1013 in an upward vertical orientation. The band 1093 can also be configured to be lifted and/or stretched upwards such that the outlet port 1013 can be transitioned from the upward retained position to a position where it extends outwardly and/or downwardly for drainage. In other embodiments, the band 1093 may include portions coupled to and extending from each of the fluid compartments, 1021, 1022. The portions may be selectively coupled using any suitable fastener, such as a button, a snap, adhesive, hook-and-loop material, etc.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially perpendicular" is recited with respect to a feature, it is understood that in further embodiments, the feature can have a precisely perpendicular configuration.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A bodily fluid drainage assembly, comprising:
   a first fluid compartment;
   a second fluid compartment in fluid communication with the first fluid compartment, wherein the first and second fluid compartments are configured to be parallel to one another when in assembled configuration;
   at least one discontinuous seam disposed between the first fluid compartment and the second fluid compartment, the at least one discontinuous seam defining a plurality of channels providing the fluid communication between the first fluid compartment and the second fluid compartment; and
   a hanger configured to suspend the bodily fluid drainage assembly from a support.

2. The bodily fluid drainage assembly of claim 1, wherein the at least one discontinuous seam includes two discontinuous seams spaced from one another and disposed between the first fluid compartment and the second fluid compartment, each of the two discontinuous seams defining a plurality of channels providing the fluid communication between the first fluid compartment and the second fluid compartment.

3. The bodily fluid drainage assembly of claim 2, further comprising an outlet tube disposed between the two discontinuous seams, wherein the outlet tube is configured to be disposed and selectively retained in an upright configuration between the two discontinuous seams when the outlet tube section is folded inwardly, and wherein the outlet tube is disposed in a downward configuration when the outlet tube section is extended outward.

4. The bodily fluid drainage assembly of claim 1, further comprising:
   a first cover coupled to the first fluid compartment and configured to obscure observation of at least a portion of a bodily fluid through a first panel of the first fluid compartment when the bodily fluid is retained within the first fluid compartment; and
   a second cover coupled to the second fluid compartment and configured to obscure observation of at least a portion of the bodily fluid through a second panel of the second fluid compartment when the bodily fluid is retained within the second fluid compartment.

5. The bodily fluid drainage assembly of claim 4, wherein the first and second panels of the fluid bag are transparent or translucent.

6. The bodily fluid drainage assembly of claim 4, wherein the first and second covers each comprise at least one volume indicator.

7. The bodily fluid drainage assembly of claim 4, wherein the first and second covers are configured such that at least a portion of each cover is removable from the assembly.

8. The bodily fluid drainage assembly of claim 4, wherein the first cover is coupled to the fluid drainage assembly at an upper end of first fluid compartment, and wherein a lower end of the first cover can be displaced so as to transition the cover from the obscuring orientation to a viewing orientation.

9. The bodily fluid drainage assembly of claim 1, wherein the first fluid compartment further comprises:
an inlet port configured to couple to a drainage tube and configured to receive drainage fluid from the drainage tube.

10. The bodily fluid drainage assembly of claim 9, further comprising an elbow connector, wherein the elbow connector is coupled to the drainage tube and rotationally coupled to the inlet port.

11. The bodily fluid drainage assembly of claim 1, further comprising an outlet tube, wherein the outlet tube is disposed on an outlet tube section that is configured to extend outwardly from the first and second fluid compartments.

12. The bodily fluid drainage assembly of claim 11, wherein the outlet tube is configured to be disposed and selectively retained in an upright configuration between the first fluid compartment and the second fluid compartment with the outlet tube oriented towards the hanger when the outlet tube section is folded inwardly, and wherein the outlet tube is disposed in a downward configuration when the outlet tube section is extended outward.

13. The bodily fluid drainage assembly of claim 12, wherein at least one of the first fluid compartment or the second fluid compartment comprises a retention member configured to retain the outlet tube in the upright configuration between the first fluid compartment and the second fluid compartment.

14. A bodily fluid drainage assembly, comprising:
a first fluid compartment;
a second fluid compartment in fluid communication with the first fluid compartment, wherein the first and second fluid compartments are configured to be parallel to one another when in an assembled configuration;
at least one discontinuous seam disposed between the first fluid compartment and the second fluid compartment, the at least one discontinuous seam defining a plurality of channels providing the fluid communication between the first fluid compartment and the second fluid compartment;
a hanger configured to suspend the bodily fluid drainage assembly from a support; and
a first cover configured to obscure observation of at least a portion of a bodily fluid through a first panel of the first fluid compartment when the bodily fluid is retained within the first fluid compartment.

15. The bodily fluid drainage assembly of claim 14, wherein at least one discontinuous seam includes two discontinuous seams spaced from one another and disposed between the first fluid compartment and the second fluid compartment, each of the two discontinuous seams defining a plurality of channels providing the fluid communication between the first fluid compartment and the second fluid compartment.

16. The bodily fluid drainage assembly of claim 14, further comprising:
a second cover coupled to the second fluid compartment and configured to obscure observation of at least a portion of the bodily fluid through a second panel of the second fluid compartment when the bodily fluid is retained within the second fluid compartment.

17. The bodily fluid drainage assembly of claim 14, wherein the first cover comprises a slip cover that is configured to cover at least a portion of the first and second fluid compartments.

18. The bodily fluid drainage assembly of claim 14, wherein the first cover comprises at least one volume indicator.

19. The bodily fluid drainage assembly of claim 14, wherein a lower end of the first cover can be displaced so as to transition the cover from the obscuring orientation to a viewing orientation.

* * * * *